(12) United States Patent
Sawada et al.

(10) Patent No.: US 8,236,841 B2
(45) Date of Patent: Aug. 7, 2012

(54) FUSED HETEROCYCLE DERIVATIVE

(75) Inventors: Takashi Sawada, Sunto-gun (JP); Naoto Osakada, Sunto-gun (JP); Satoshi Kaneko, Sunto-gun (JP); Atsuko Mizutani, Sunto-gun (JP); Noriaki Uesaka, Sunto-gun (JP); Keishi Katayama, Mishima (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 522 days.

(21) Appl. No.: 12/310,926

(22) PCT Filed: Sep. 13, 2007

(86) PCT No.: PCT/JP2007/067793
§ 371 (c)(1),
(2), (4) Date: May 1, 2009

(87) PCT Pub. No.: WO2008/032764
PCT Pub. Date: Mar. 20, 2008

(65) Prior Publication Data
US 2009/0239853 A1 Sep. 24, 2009

(30) Foreign Application Priority Data
Sep. 13, 2006 (JP) ................. 2006-247578

(51) Int. Cl.
A01N 43/52 (2006.01)
A01N 43/54 (2006.01)
A01N 43/90 (2006.01)
A61K 31/415 (2006.01)
A61K 31/517 (2006.01)
A61K 31/519 (2006.01)
C07D 235/00 (2006.01)
C07D 487/00 (2006.01)

(52) U.S. Cl. ................. 514/394; 514/258.1; 548/304.4; 544/281

(58) Field of Classification Search .......... 514/394, 514/258.1; 548/304.4; 544/281
See application file for complete search history.

(56) References Cited

U.S. PATENT DOCUMENTS

| | | | |
|---|---|---|---|
| 5,420,138 A | 5/1995 | Corbier et al. | |
| 5,650,414 A | 7/1997 | Corbier et al. | |
| 5,691,347 A | 11/1997 | Corbier et al. | |
| 6,348,474 B1 | 2/2002 | Kayakiri et al. | |
| 6,653,304 B2 | 11/2003 | Leftheris et al. | |
| 7,407,968 B2 | 8/2008 | Page et al. | |
| 2002/0119972 A1 | 8/2002 | Leftheris et al. | |
| 2004/0142961 A1 | 7/2004 | Sundermann et al. | |
| 2005/0049419 A1 | 3/2005 | Wallace et al. | |
| 2005/0054701 A1 | 3/2005 | Wallace et al. | |
| 2005/0239822 A1 | 10/2005 | Hennies et al. | |
| 2005/0239823 A1 | 10/2005 | Oberboersch et al. | |
| 2005/0288356 A1 | 12/2005 | Barth et al. | |
| 2006/0030610 A1 | 2/2006 | Koch et al. | |
| 2006/0148801 A1 | 7/2006 | Hsieh et al. | |
| 2006/0281750 A1 | 12/2006 | Li et al. | |
| 2006/0293354 A1 | 12/2006 | Eatherton | |
| 2007/0105893 A1 | 5/2007 | Page et al. | |
| 2008/0103139 A1 | 5/2008 | Ishizuka et al. | |
| 2008/0312435 A1 | 12/2008 | Saito et al. | |

FOREIGN PATENT DOCUMENTS

| | | |
|---|---|---|
| EP | 0 356 234 | 2/1990 |
| GB | 991 589 | 5/1965 |
| JP | 2004-529141 | 9/2004 |
| JP | 2006/501228 | 1/2006 |
| JP | 2006-505568 | 2/2006 |
| JP | 2006/509781 | 3/2006 |
| WO | 99/00372 | 1/1999 |
| WO | 01/58869 | 8/2001 |
| WO | 02/02557 | 1/2002 |
| WO | 02/066477 | 8/2002 |
| WO | 02/066478 | 8/2002 |
| WO | WO 02066477 A2 * | 8/2002 |
| WO | 2004/033453 | 4/2004 |
| WO | 2004/035548 | 4/2004 |
| WO | 2004/035578 | 4/2004 |
| WO | 2006/046778 | 5/2006 |

(Continued)

OTHER PUBLICATIONS

Supplementary European Search Report dated Sep. 10, 2010 in Application No. EP 07 80 7200.

(Continued)

*Primary Examiner* — Shengjun Wang
*Assistant Examiner* — Kendra D Carter
(74) *Attorney, Agent, or Firm* — Wenderoth, Lind & Ponack, L.L.P.

(57) ABSTRACT

A fused heterocycle derivative represented by the general formula (I):

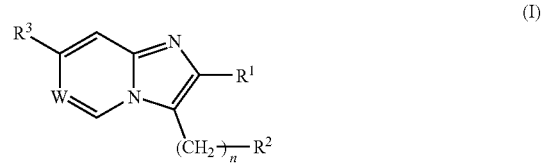

(wherein $R^1$ represents optionally substituted lower alkyl, or the like; $R^2$ represents an optionally substituted aliphatic heterocyclic group, or the like; $R^3$ represents —C(=Z)NR⁵R⁶ (wherein $R^5$ and $R^6$ represent optionally substituted lower alkyl, or the like, and Z represents an oxygen atom or the like), or the like; n represents an integer of 1 to 3; and W represents C—$R^5$ (wherein $R^5$ represents a hydrogen atom or the like)) or a pharmaceutically acceptable salt thereof, and the like are provided.

14 Claims, No Drawings

FOREIGN PATENT DOCUMENTS

| | | |
|---|---|---|
| WO | 2006/051704 | 5/2006 |
| WO | 2006/094235 | 9/2006 |
| WO | WO 2006094235 A1 * | 9/2006 |

OTHER PUBLICATIONS

D.L. Hertzog, "Recent advances in the cannabinoids", Expert Opin. Ther. Patents, vol. 14, No. 10, pp. 1435-1452, 2004.

International Search Report issued Oct. 30, 2007 in the International (PCT) Application of which the present application is the U.S. National Stage.

D. L. Hertzog, "Recent advances in the cannabinoids", Expert Opin. Ther. Patents, vol. 14, No. 10, pp. 1435-1452, 2004.

* cited by examiner

FUSED HETEROCYCLE DERIVATIVE

This application is a U.S. national stage of International Application No. PCT/P2007/067793 filed Sep. 13, 2007.

TECHNICAL FIELD

The present invention relates to a cannabinoid type 2 (CB2) receptor modulator comprising a fused heterocycle derivative or a pharmaceutically acceptable salt thereof as an active ingredient, and a fused heterocycle derivative or a pharmaceutically acceptable salt thereof which has an effect to modulate a CB2 receptor and is useful as a therapeutic and/or preventive agent for a pain, or the like.

BACKGROUND ART

Cannabinoids are substances isolated as biologically active components of marijuana, and have an antiemetic effect, an intraocular pressure lowering effect, an anticonvulsant effect, an analgesic effect, an orexigenic effect, a bronchodilator effect, an anti-asthmatic effect, an anti-inflammatory effect, an anti-anxiety effect, a sedative effect, a psychotropic effect and the like.

It is known that there are two subtypes of cannabinoid receptors, type 1 (CB1) receptors [Nature, vol. 346, p. 561 (1990)] and type 2 (CB2) receptors.

The CB1 receptors are distributed predominantly in the central nervous system such as brain, and it has been considered that the central effects of cannabinoids such as sedative effect and psychotropic effect are mediated by CB1 receptors. Further, because it has also been confirmed that the CB1 receptors are distributed in tissues which participate in the nociceptive signal transduction such as the dorsal horn of the spinal cord and the dorsal root ganglion neuron (DRG) [Neuroscience, vol. 92, p. 1171 (1999); Molecular and cellular neurosciences, vol. 15, p. 510 (2000)], it has been considered that the analgesic effects of cannabinoids are mediated by CB1 receptors.

On the other hand, it has been confirmed that the CB2 receptors are distributed in the spleen, lymph nodes, and also white blood cells, B cells, T cells, macrophages, mast cells and the like. Because the CB2 receptors are abundantly distributed mainly in tissues and cells of the immune system including hematopoietic cells, it has been considered that the anti-asthmatic effect and anti-inflammatory effect of cannabinoids are mediated by CB2 receptors [Nature, vol. 365, p. 61 (1993); British Journal of Pharmacology, vol. 139, p. 775 (2003)]. In addition, it has been reported that CB2 receptor-selective agonists show a peripheral analgesic effect [Pain, vol. 93, p. 239 (2001); Proceedings of the National Academy of Science of the United States of America, vol. 102, p. 3093 (2005)] and a central analgesic effect [European Journal of Neuroscience, vol. 17, p. 2750 (2003); European Journal of Neuroscience, vol. 22, p. 371 (2005); European Journal of Neuroscience, vol. 23, p. 1530 (2006)], and it has been revealed that the analgesic effects of cannabinoids are also mediated by CB2 receptors. Further, as CB2 receptor-mediated effects, an antipruritic effect (WO2002/065997, WO2003/035109, WO2003/070277, WO2006/046778), an inhibitory effect on osteoclast proliferation and activity [Proceedings of the National Academy of Science of the United States of America, vol. 103, p. 696 (2006)] and the like have also been reported recently.

As described above, as the elucidation of the function of cannabinoid receptors has been progressing, among the modulators of cannabinoid receptor functions, a medicament which does not have effects mediated by the CB1 receptors, that is, central effects such as sedative effect and psychotropic effect have been expected as an excellent medicament without side effects specific to cannabinoids. That is, a CB2 receptor-selective modulator has been expected to be useful as a therapeutic and/or preventive agent for various diseases associated with CB2 receptors without side effects specific to cannabinoids. In particular, CB2-selective agonists have been expected as, for example, therapeutic and/or preventive agents for pains (such as neuropathic pain, trigeminal neuralgia, diabetic pain, postherpetic neuralgia, neuropathic low back pain, HIV-related pain, fibromyalgia, cancer pain, inflammatory pain, acute pain, chronic pain, postoperative pain, acute pain after tooth extraction, chronic musculoskeletal pain, noxious pain, psychogenic pain, and menstrual pain), migraine, pruritus, inflammation, allergies, immunodeficiency, autoimmune diseases, chronic rheumatoid arthritis, osteoarthritis, inflammatory bowel disease, irritable bowel syndrome, multiple sclerosis, asthma (such as airway inflammatory cell infiltration, airway hyperresponsiveness, bronchoconstriction, and mucus hypersecretion), chronic obstructive lung disease, emphysema, pulmonary fibrosis, coughing, allergic rhinitis, dermatitis, atopic dermatitis, arteriosclerosis, glaucoma, anorexia, osteoporosis, and the like.

As the CB2 receptor modulator, for example, a large number of compounds such as indole derivatives, benzimidazole derivatives, sulfonamide derivatives, thiazine derivatives, pyrimidine derivatives, imine derivatives, and pyridone derivatives (see, for example, Non-patent document 1, Patent documents 1, 2, and 3, etc.). Further, imidazole derivatives having a carbamoyl group at the 4-position are also known (see Patent document 4).

Meanwhile, as imidazopyridine derivatives, imidazo[1,2-a]pyridine derivatives having arylamino at the 7-position (see Patent documents 5, 6, and 7), imidazo[1,2-a]pyridine derivatives having aryl in the 2- or 3-position (see Patent documents 8 and 11), and the like are known. Further, imidazo[1,2-a]pyridine derivatives having aminoalkyl at the 3-position (see Patent documents 9 and 10), imidazo[1,2-a]pyridine derivatives having aralkyl at the 3-position (see Patent documents 12 to 14), and further imidazo[1,2-a]pyridine derivatives having alkyl at the 3-position (see Patent document 15), and the like are known. And imidazo[1,2-a]pyridine derivatives having cycloalkylamino or aralkylamino at the 3-position (see Patent documents 16), and imidazo[1,2-a]pyridine derivatives having aralkyl or aroyl at the 3-position (see Patent documents 17) are known.

Patent document 1: WO 2004/035548
Patent document 2: WO 2006/051704
Patent document 3: WO 2006/046778
Patent document 4: WO 2001/58869
Patent document 5: U.S. Published Unexamined Patent Application No. 030610/2006
Patent document 6: U.S. Published Unexamined Patent Application No. 054701/2005
Patent document 7: U.S. Published Unexamined Patent Application No. 049419/2005
Patent document 8: WO 2002/066478
Patent document 9: U.S. Published Unexamined Patent Application No. 0239822/2005
Patent document 10: U.S. Published Unexamined Patent Application No. 0239823/2005
Patent document 11: WO 2002/066477
Patent document 12: U.S. Pat. No. 5,420,138
Patent document 13: U.S. Pat. No. 5,650,414
Patent document 14: U.S. Pat. No. 5,691,347

Patent document 15: U.S. Published Unexamined Patent Application No. 2006/0281750
Patent document 16: WO 2006/094235
Patent document 17: U.S. Published Unexamined Patent Application No. 0148801/2006
Non-patent document 1: "Expert Opin. Ther. Patents.", 2004, vol. 14, p. 1435

DISCLOSURE OF THE INVENTION

Problems to be Solved by the Invention

An object of the present invention is to provide a CB2 receptor modulator, a CB2 receptor agonist, and the like which comprise a fused heterocycle derivative or a pharmaceutically acceptable salt thereof as an active ingredient. Another object is to provide a novel fused heterocycle derivative or a pharmaceutically acceptable salt thereof which has an effect to modulate a CB2 receptor and is useful, for example, as a CB2 receptor agonist, a therapeutic and/or preventive agent for a pain, or the like.

Means for Solving the Problems

The present invention relates to the following (1) to (22).
(1) A fused heterocycle derivative represented by the general formula (I):

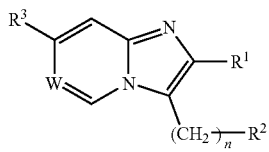

(wherein $R^1$ represents optionally substituted lower alkyl, optionally substituted lower alkenyl, optionally substituted cycloalkyl, an optionally substituted aliphatic heterocyclic group, or optionally substituted aralkyl;
$R^2$ represents optionally substituted cycloalkyl, optionally substituted aryl, an optionally substituted heteroaromatic group, or an optionally substituted aliphatic heterocyclic group;
$R^3$ represents (i) —C(=Z)$R^4$
(wherein $R^4$ represents optionally substituted lower alkyl, optionally substituted lower alkenyl, optionally substituted cycloalkyl, optionally substituted aralkyl, optionally substituted aryl, an optionally substituted heteroaromatic group, or an optionally substituted aliphatic heterocyclic group, and Z represents an oxygen atom or a sulfur atom),
(ii) —C(=Z)NR$^5$R$^6$
(wherein $R^5$ and $R^6$ may be the same or different and each represents a hydrogen atom, optionally substituted lower alkyl, optionally substituted lower alkenyl, optionally substituted cycloalkyl, optionally substituted aralkyl, optionally substituted aryl, an optionally substituted heteroaromatic group, or an optionally substituted aliphatic heterocyclic group or $R^5$ and $R^6$ together with the adjacent nitrogen atom thereto form an optionally substituted nitrogen-containing heterocyclic group, and Z has the same definition as described above), or
(iii) —NR$^7$R$^8$
(wherein $R^7$ and $R^8$ may be the same or different and each represents a hydrogen atom, optionally substituted lower alkyl, optionally substituted cycloalkyl, optionally substituted aralkyl, an optionally substituted aliphatic heterocyclic group, —C(=O)R$^9$
(wherein $R^9$ represents optionally substituted lower alkyl, optionally substituted aryl, or an optionally substituted heteroaromatic group), —C(=O)NR$^{10}$R$^{11}$
(wherein $R^{10}$ and $R^{11}$ may be the same or different and each represents a hydrogen atom or optionally substituted lower alkyl), —SO$_2$R$^{12}$
(wherein $R^{12}$ represents optionally substituted lower alkyl, optionally substituted aryl, or an optionally substituted heteroaromatic group), or —SO$_2$NR$^{13}$R$^{14}$
(wherein $R^{13}$ and $R^{14}$ may be the same or different and each represents a hydrogen atom, optionally substituted lower alkyl, optionally substituted aryl, or an optionally substituted heteroaromatic group));
n represents an integer of 1 to 3; and
W represents a nitrogen atom or C—R$^{15}$
(wherein $R^{15}$ represents a hydrogen atom, halogen or lower alkyl)),
or a pharmaceutically acceptable salt thereof.
(2) The fused heterocycle derivative or the pharmaceutically acceptable salt thereof according to (1), wherein $R^1$ is optionally substituted lower alkyl, or optionally substituted cycloalkyl.
(3) The fused heterocycle derivative or the pharmaceutically acceptable salt thereof according to (1), wherein $R^1$ is optionally substituted tertiary lower alkyl, or optionally substituted tertiary cycloalkyl.
(4) The fused heterocycle derivative or the pharmaceutically acceptable salt thereof according to (1), wherein $R^1$ is optionally substituted lower alkyl.
(5) The fused heterocycle derivative or the pharmaceutically acceptable salt thereof according to (1), wherein $R^1$ is tert-butyl.
(6) The fused heterocycle derivative or the pharmaceutically acceptable salt thereof according to any one of (1) to (5), wherein $R^3$ is —C(=Z)$R^{4a}$ (wherein $R^{4a}$ represents optionally substituted lower alkyl, optionally substituted aryl, or an optionally substituted aliphatic heterocyclic group, and Z has the same definitions as described above), or is —C(=Z)NR$^5$R$^6$ (wherein $R^5$, $R^6$ and Z have the same definitions as described above, respectively).
(7) The fused heterocycle derivative or the pharmaceutically acceptable salt thereof according to any one of (1) to (5), wherein $R^3$ is —C(=Z) NR$^5$R$^6$ (wherein $R^5$, $R^6$ and Z have the same definitions as described above, respectively).
(8) The fused heterocycle derivative or the pharmaceutically acceptable salt thereof according to any one of (1) to (5), wherein $R^3$ is —C(=Z) NR$^{5a}$R$^{6a}$ (wherein $R^{5a}$ and $R^{6a}$ may be the same or different and each represents a hydrogen atom or optionally substituted lower alkyl or $R^{5a}$ and $R^{6a}$ together with the adjacent nitrogen atom thereto form an optionally substituted nitrogen-containing heterocyclic group).
(9) The fused heterocycle derivative or the pharmaceutically acceptable salt thereof according to any one of (1) to (8), wherein Z is an oxygen atom.
(10) The fused heterocycle derivative or the pharmaceutically acceptable salt thereof according to any one of (1) to (9), wherein n is 1.
(11) The fused heterocycle derivative or the pharmaceutically acceptable salt thereof according to any one of (1) to (10), wherein $R^2$ is an optionally substituted aliphatic heterocyclic group.
(12) The fused heterocycle derivative or the pharmaceutically acceptable salt thereof according to any one of (1) to (11), wherein W is a nitrogen atom.

(13) The fused heterocycle derivative or the pharmaceutically acceptable salt thereof according to any one of (1) to (11), wherein W is CH.

(14) A CB2 receptor modulator comprising the fused heterocycle derivative or the pharmaceutically acceptable salt thereof described in any one of (1) to (13) as an active ingredient.

(15) The modulator according to (14), wherein the modulator is an agonist.

(16) A therapeutic and/or preventive agent for a pain comprising the fused heterocycle derivative or the pharmaceutically acceptable salt thereof described in any one of (1) to (13) as an active ingredient.

(17) A method for modulating a CB2 receptor characterized by administering an effective amount of the fused heterocycle derivative or the pharmaceutically acceptable salt thereof described in any one of (1) to (13).

(18) The method according to (17), wherein the modulating a CB2 receptor is agonizing a CB2 receptor.

(19) A method for treating and/or preventing a pain characterized by administering an effective amount of the fused heterocycle derivative or the pharmaceutically acceptable salt thereof described in any one of (1) to (13).

(20) Use of the fused heterocycle derivative or the pharmaceutically acceptable salt thereof described in any one of (1) to (13) for the manufacture of a CB2 receptor modulator.

(21) The use according to (20), wherein the modulator is an agonist.

(22) Use of the fused heterocycle derivative or the pharmaceutically acceptable salt thereof described in any one of (1) to (13) for the manufacture of a therapeutic and/or preventive agent for a pain.

EFFECT OF THE INVENTION

According to the present invention, a CB2 receptor modulator (for example, a CB2 receptor agonist etc.) and the like comprising a fused heterocycle derivative or a pharmaceutically acceptable salt thereof as an active ingredient are provided. Further, a novel fused heterocycle derivative or a pharmaceutically acceptable salt thereof which has an effect to modulate a CB2 receptor and is useful, for example, as a CB2 receptor agonist, a therapeutic and/or preventive agent for a pain, or the like is provided.

BEST MODE FOR CARRYING OUT THE INVENTION

Hereinafter, the compound represented by the general formula (I) is referred to as Compound (I). The compounds having the other formula numbers are referred to in the same manner.

The definitions of the respective groups in the general formulae (I) are as follows.

Examples of the lower alkyl include linear or branched alkyl having 1 to 10 carbon atoms. More specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, and the like. Examples of the tertiary lower alkyl include tert-butyl, tert-pentyl, 1,1-dimethylbutyl, 1,1,2-trimethyl propyl, and the like.

Examples of the lower alkenyl include linear or branched alkenyl having 2 to 10 carbon atoms. More specific examples thereof include vinyl, allyl, 1-propenyl, butenyl, pentenyl, hexenyl, heptenyl, octenyl, nonenyl, decenyl, and the like.

Examples of the cycloalkyl include cycloalkyl having 3 to 8 carbon atoms, bridged cycloalkyl having 4 to 8 carbon atoms, and bicyclic or tricyclic spiro cycloalkyl in which cycloalkyl having 3 to 8 carbon atoms are spiro bonded. More specific examples thereof include cyclopropyl, cyclobutyl, cyclopentyl, cyclohexyl, cycloheptyl, cyclooctyl, adamantyl, noradamantyl, bicyclo[2.2.1]heptyl, spiro[4.5]decanyl, and the like. Examples of the tertiary cycloalkyl include 1-adamantyl, 1-methylcyclopropyl, 1-methylcyclohexyl, and the like.

Examples of the aralkyl include aralkyl having 7 to 16 carbon atoms. More specific examples include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl, and the like.

Examples of the aryl include aryl having 6 to 14 carbon atoms. More specific examples include phenyl, naphthyl, azulenyl, anthryl, and the like.

Examples of the aliphatic heterocyclic group include a 5- or 6-membered monocyclic aliphatic heterocyclic group which contains at least one atom selected from a nitrogen atom, an oxygen atom, and a sulfur atom, a bicyclic or tricyclic condensed aliphatic heterocyclic group in which 3- to 8-membered rings are fused and contains at least one atom selected from a nitrogen atom, an oxygen atom and a sulfur atom, and the like. More specific examples thereof include aziridinyl, azetidinyl, pyrrolidinyl, pyrrolyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, tetrahydrothiophenyl, tetrahydro-2H-thiopyranyl, oxazolidinyl, morpholino, morpholinyl, thioxazolidinyl, thiomorpholinyl, 1-oxo-thiomorpholinyl, 1,1-dioxothiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dioxepanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, and the like.

Examples of the heteroaromatic group include a 5- or 6-membered monocyclic heteroaromatic group which contains at least one atom selected from a nitrogen atom, an oxygen atom and a sulfur atom, a bicyclic or tricyclic condensed heteroaromatic group in which 3- to 8-membered rings are fused and contains at least one atom selected from a nitrogen atom, an oxygen atom and a sulfur atom, and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, and the like.

Examples of the nitrogen-containing heterocyclic group formed together with the adjacent nitrogen atom thereto include a 5- or 6-membered monocyclic heterocyclic group which contains at least one nitrogen atom (the monocyclic heterocyclic group may further contain another nitrogen atom, an oxygen atom or a sulfur atom), a bicyclic or tricyclic condensed heterocyclic group in which 3- to 8-membered rings are fused and contains at least one nitrogen atom (the condensed heterocyclic group may further contain another nitrogen atom, an oxygen atom or a sulfur atom), and the like. More specific examples thereof include aziridinyl, azetidinyl, pyrrolidinyl, piperidino, azepanyl, pyrrolyl, pyrrolinyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, 1-oxo-thiomorpholinyl, 1,1-dioxo-thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridinyl pyrrolopyrimidinyl, imidazopyridinyl, purinyl, and the like.

The halogen refers to each atom of fluorine, chlorine, bromine, and iodine.

The sulfanyl refers to —SH.

Examples of the substituents for the optionally substituted lower alkyl, the optionally substituted tertiary lower alkyl, and the optionally substituted lower alkenyl, which may be the same or different and 1 to 3 in number, include substituents selected from the group consisting of halogen, hydroxy, sulfanyl, nitro, cyano, carboxy, carbamoyl, $C_{3-8}$ cycloalkyl, an aliphatic heterocyclic group, a heteroaromatic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ may be the same or different and each represents a hydrogen atom, $C_{1-10}$ alkyl, $C_{3-8}$ cycloalkyl, $C_{6-14}$ aryl, a heteroaromatic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di($C_{1-10}$ alkyl) carbamoyl.

Examples of the substituents for the optionally substituted aralkyl, the optionally substituted aryl, and the optionally substituted heteroaromatic group, which may be the same or different and 1 to 3 in number, include substituents selected from the group consisting of halogen, hydroxy, sulfanyl, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, a heteroaromatic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ have the same definitions as described above, respectively), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl and di($C_{1-10}$ alkyl) carbamoyl.

Examples of the substituents for the optionally substituted cycloalkyl, the optionally substituted tertiary cycloalkyl, the optionally substituted aliphatic heterocyclic group, and the optionally substituted nitrogen-containing heterocyclic group formed together with the adjacent nitrogen atom thereto, which may be the same or different and 1 to 3 in number, include substituents selected from the group consisting of oxo, halogen, hydroxy, sulfanyl, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, a heteroaromatic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ have the same definitions as described above, respectively), $C_{2-11}$ alkanoyl, $C_{7-35}$ aroyl, $C_{1-10}$ alkoxycarbonyl, $C_{6-14}$ aryloxycarbonyl, $C_{1-10}$ alkylcarbamoyl and di($C_{1-10}$ alkyl) carbamoyl.

Examples of the $C_{1-10}$ alkyl and the $C_{1-10}$ alkyl moieties of the $C_{1-10}$ alkoxy, the $C_{2-11}$ alkanoyloxy, the $C_{1-10}$ alkylsulfanyl, the $C_{2-11}$ alkanoyl, the $C_{1-10}$ alkoxycarbonyl, the $C_{1-10}$ alkylcarbamoyl and di($C_{1-10}$ alkyl)carbamoyl described above include the groups illustrated for the above-mentioned lower alkyl. The two $C_{1-10}$ alkyl moieties of the di($C_{1-10}$ alkyl)carbamoyl may be the same or different from each other.

Examples of the $C_{3-8}$ cycloalkyl and the cycloalkyl moieties of the $C_{3-8}$ cycloalkoxy include the groups illustrated for the above-mentioned cycloalkyl.

Examples of the $C_{6-14}$ aryl and the aryl moieties of the $C_{6-14}$ aryloxy, the $C_{7-15}$ aroyl, the $C_{7-15}$ aroyloxy and the $C_{6-14}$ aryloxycarbonyl include the groups illustrated for the above-mentioned aryl.

Examples of the $C_{7-16}$ aralkyl and the aralkyl moieties of the $C_{7-16}$ aralkyloxy and $C_{7-16}$ aralkyloxycarbonyl include the groups illustrated for the above-mentioned aralkyl.

Examples of the aliphatic heterocyclic group and the heteroaromatic group include the groups illustrated for the above-mentioned aliphatic heterocyclic group and heteroaromatic group, respectively. The halogen is the same definition as described above.

The respective groups of Compound (I) are as follows.

As $R^1$, for example, lower alkyl which may have 1 to 3 substituents selected from the group consisting of halogen, hydroxyl, and $C_{1-10}$ alkoxy is preferred. More specifically, for example, methyl, ethyl, propyl, 2-propyl, butyl, 2-butyl, tert-butyl, pentyl, 2-pentyl, 3-pentyl, 1,1-dimethylpropyl, hexyl, 2-hexyl, 3-hexyl, 3-methyl-3-pentyl, 2-methyl-2-pentyl, 3-methyl-3-hexyl, 2-methyl-2-hexyl, 3-ethyl-3-hexyl, and the like are preferred, and $C_{1-10}$ alkyl groups having a quaternary carbon such as tert-butyl, 1,1-dimethylpropyl, 3-methyl-3-pentyl, 2-methyl-2-pentyl, 3-methyl-3-hexyl, 2-methyl-2-hexyl and 3-ethyl-3-hexyl are preferred, and tert-butyl, 1,1-dimethylpropyl, and the like are more preferred, and tert-butyl and the like are further more preferred.

As $R^2$, for example, cycloalkyl, an aliphatic heterocyclic group, and the like are preferred. As the cycloalkyl, for example, cyclopentyl, cyclohexyl, cycloheptyl, and the like are preferred, and cyclohexyl and the like are more preferred. As the aliphatic heterocyclic group, for example, tetrahydrofuranyl, tetrahydrothiophenyl, tetrahydro-2H-pyranyl, tetrahydro-2H-thiopyranyl, morpholinyl, thiomorpholinyl, 5,6-dihydro-2H-pyranyl, dioxepanyl, and the like are preferred, and tetrahydro-2H-pyranyl and the like are more preferred. Such cycloalkyl and aliphatic heterocyclic group may have 1 to 3 substituents, and as the substituent, for example, cyano, halogen, hydroxy, $C_{1-10}$ alkoxy, $C_{1-10}$ alkyl, oxo, and the like are preferred, and cyano, a fluorine atom, a chlorine atom, an iodine atom, hydroxy, methoxy, ethoxy, propoxy, isopropoxy, methyl, ethyl, propyl, isopropyl, oxo, and the like are more preferred, and cyano, a fluorine atom, a chlorine atom, an iodine atom, hydroxy, methoxy, methyl, oxo, and the like are further more preferred.

Preferably, n is for example, 1 or 2, and more preferably 1.

Examples of the pharmaceutically acceptable salt of Compound (I) include pharmaceutically acceptable acid addition salts, metal salts, ammonium salts, organic amine addition salts, amino acid addition salts, and the like. Examples of the pharmaceutically acceptable acid addition salts of Compound (I) include inorganic acid salts such as hydrochlorides, hydrobromides, nitrates, sulfates, and phosphates, organic acid salts such as acetates, oxalates, maleates, fumarates, citrates, benzoates, methanesulfonates, and the like. Examples of the pharmaceutically acceptable metal salts include alkali metal salts such as sodium salts and potassium salts, alkaline earth metal salts such as magnesium salts and calcium salts, aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

Hereinafter, production methods of Compound (I) will be described.

In the production methods described below, when a defined group changes under the conditions of the production methods or is not suitable for carrying out the production methods, it is possible to produce a desired compound using a method, which is commonly used in synthetic organic chemistry, for introducing and removing a protecting group [for example, the method described in Protective Groups in Organic Synthesis, third edition, T. W. Greene, John Wiley & Sons Inc. (1999), etc.] or the like. If necessary, the order of reaction steps such as introduction of a substituent can be changed.

The compound (I) can be produced according to the following steps.

Production Method 1

Among Compounds (I), Compound (Ia) in which $R^3$ is —C(=O) $NR^5R^6$ (wherein $R^5$ and $R^6$ have the same definitions as described above, respectively), Compound (Ib) in which $R^3$ is —C(=O)$R^4$ (wherein $R^4$ has the same definitions as described above), Compound (Ic) in which $R^3$ is —$NHR^7$, and Compound (Id) in which $R^3$ is —$NR^7R^8$, can be produced according to the following steps.

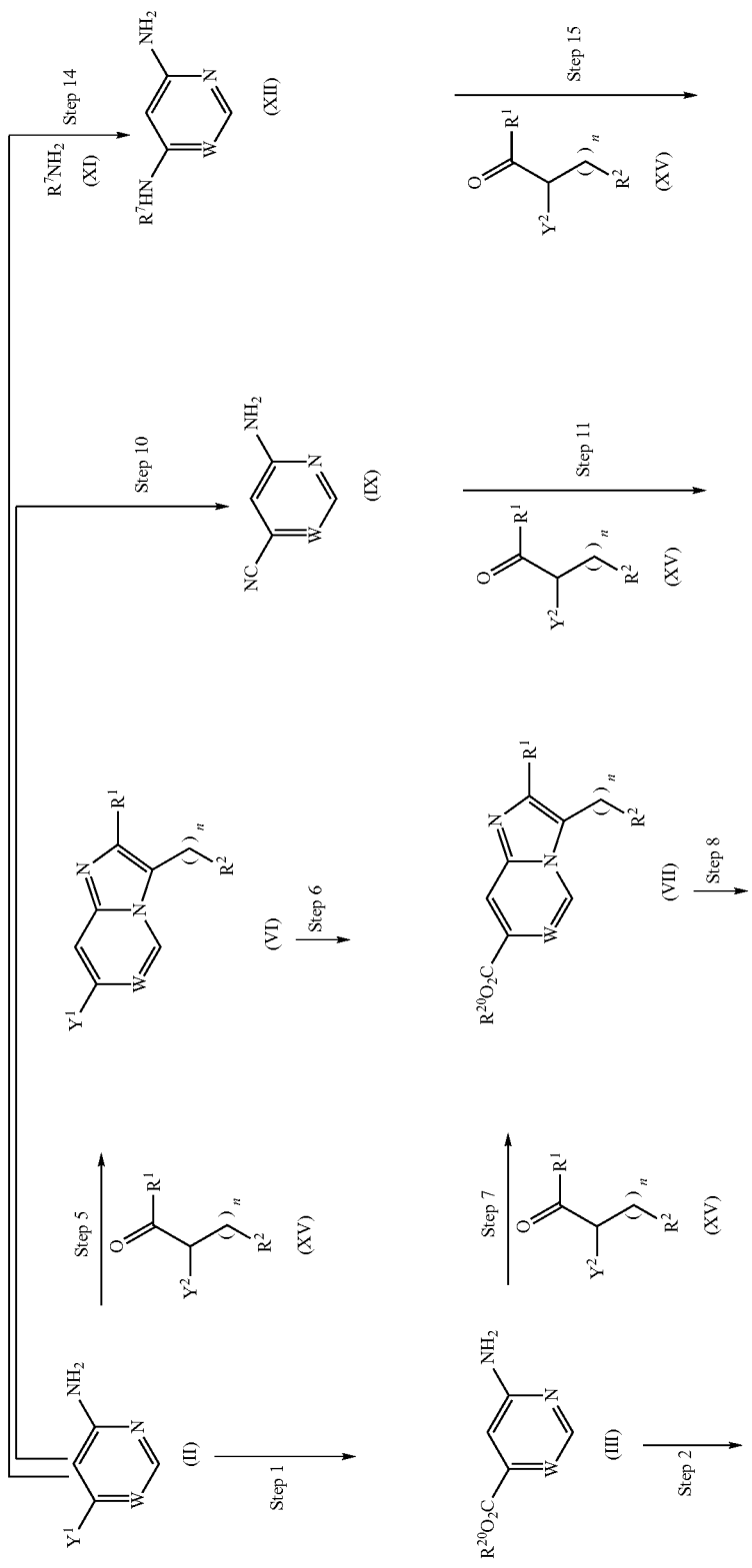

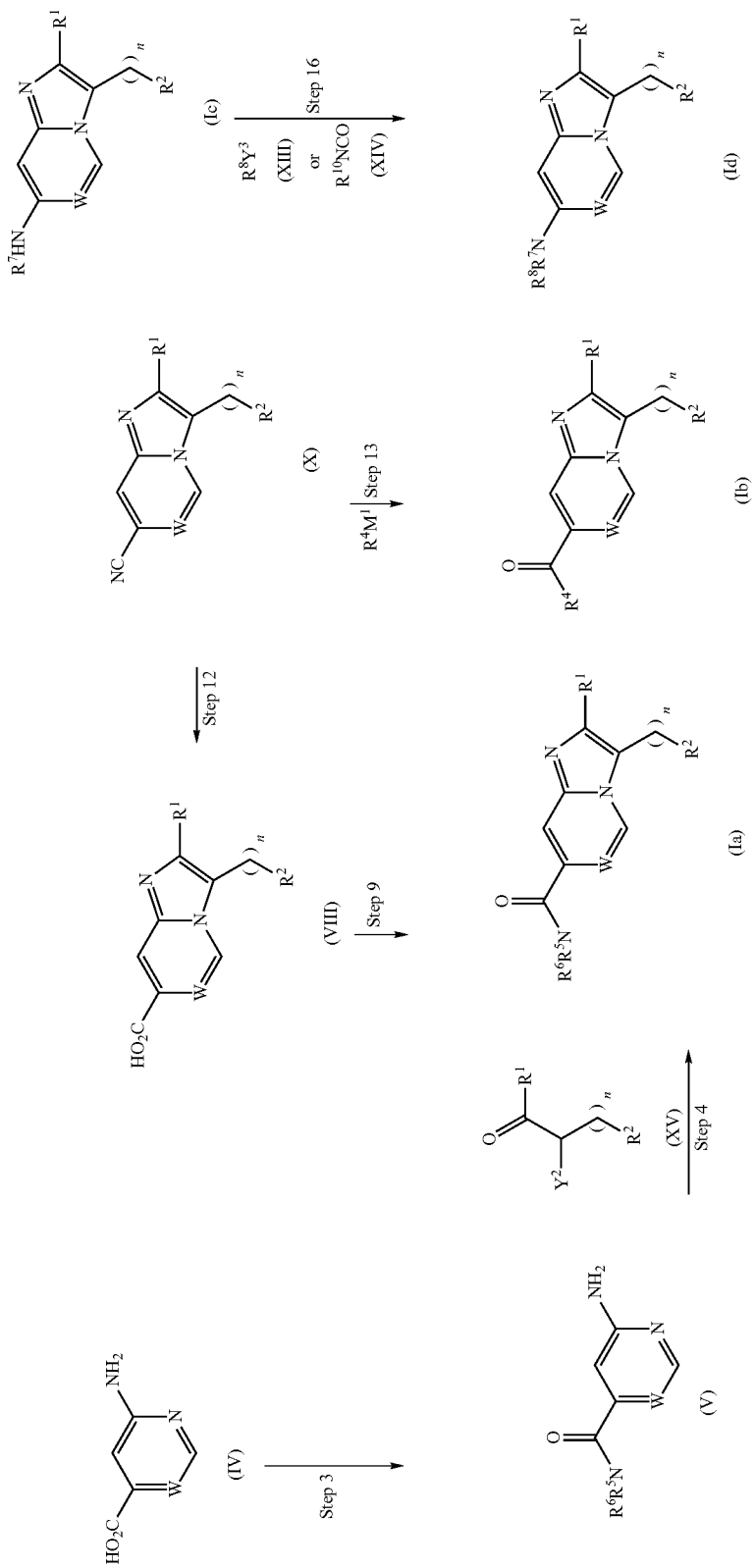

(wherein $Y^1$, $Y^2$ and $Y^3$ independently represent a chlorine atom, a bromine atom or an iodine atom, $R^1$, $R^2$, $R^4$, $R^5$, $R^6$, $R^7$, $R^8$, $R^{10}$, n and W have the same definitions as described, respectively, $R^{20}$ represents $C_{1-10}$ alkyl or $C_{7-16}$ aralkyl, and $M^1$ represents a metal group such as MgBr, MgCl and Li.)

Step 1

The compound (III) can be prepared by reaction of the compound (II) in a solvent under carbon monoxide atmosphere, in the presence of $R^{20}OH$ (wherein $R^{20}$ has the same definitions as described above) of which the amount is preferably 1 Eq to a large excessive amount and in the presence of a palladium catalyst of which the amount is preferably 1 to 100 mol %, and if needed in the presence of a catalyst ligand of which the amount is preferably 1 to 100 mol % and/or if needed in the presence of a base of which the amount is preferably 1 to 10 Eq, at a temperature of −20° C. to the boiling point of the solvent to be used under normal or increased pressure for 5 minutes to 72 hours.

The base may be, for example, potassium carbonate, potassium phosphate, potassium hydroxide, triethylamine, diisopropylethylamine, N-methylmorpholine, pyridine, 1,8-diazabicyclo[5.4.0]-7-undecene (DBU), potassium acetate, sodium acetate or the like. The palladium catalyst may be, for example, palladium acetate, tetrakis(triphenylphosphine)palladium or the like. The catalyst ligand may be, for example, triphenylphosphine, 1,1'-bis(diphenylphosphino)ferrocene, 1,3-bis(diphenylphosphino)propane or the like. The solvent may be, for example, dichloromethane, chloroform, 1,2-dichloroethane, toluene, ethyl acetate, acetonitrile, diethyl ether, tetrahydrofuran (THF), 1,2-dimethoxyethane (DME), 1,4-dioxane, N,N-dimethylformamide (DMF), N,N-dimethylacetamide (DMA), N-methylpyrrolidone (NMP), water or the like. These solvents are used alone or as a mixture thereof.

The compound (II) and $R^{20}OH$ each can be obtained commercially.

Step 2

The compound (IV) can be prepared from the compound (III) by reference to, for example, a method of removing protective groups described in Protective Groups in Organic Synthesis, authored by T. W. Greene, published by John Wiley & Sons Inc. (1981) etc.

For example, when $R^{20}$ is methyl or ethyl, the compound (IV) can be prepared by reacting the compound (III) with a base of which the amount is preferably 1 Eq to a large excessive amount, in a water-containing solvent at a temperature of 0° C. to the boiling point of the solvent to be used for 5 minutes to 72 hours.

The base may be, for example, sodium hydroxide, potassium hydroxide, lithium hydroxide or the like. The solvent may be, for example, methanol, ethanol, propanol, THF, 1,4-dioxane, DME, toluene, dichloromethane, DMF or the like. A mixed solvent of water and any of these can be used.

For example, when $R^{20}$ is tert-butyl, the compound (IV) can be prepared by reacting the compound (III) with an acid of which the amount is preferably 1 Eq to a large excessive amount, in a solvent or solvent-free environment at a temperature of −30 to 100° C. for 5 minutes to 72 hours.

The acid may be, for example, hydrochloric acid, sulfuric acid, trifluoroacetic acid, methanesulfonic acid or the like. The solvent may be, for example, methanol, ethanol, propanol, THF, 1,4-dioxane, DME, toluene, ethyl acetate, dichloromethane, DMF, water or the like. These solvents are used alone or as a mixture thereof.

Step 3

The compound (V) can be prepared by reacting the compound (IV) with $HNR^5R^6$ (wherein $R^5$ and $R^6$ have the same definitions as described above) of which the amount is preferably 1 to 30 Eq, in a solvent or solvent-free environment, in the presence of a condensing agent of which the amount is preferably 1 to 30 Eq and if needed in the presence of an additive of which the amount is preferably 1 to 30 Eq, at a temperature of −30 to 150° C. for 5 minutes to 72 hours.

The condensing agent may be, for example, dicyclohexylcarbodiimide (DCC), diisopropylcarbodiimide, N-(3-dimethylaminopropyl)-N'-ethylcarbodiimide (EDC), EDC hydrochloride or the like. The additive may be, for example, 1-hydroxybenzotriazole hydrate, triethylamine, 4-dimethylaminopyridine (DMAP) or the like. These additives are used alone or as a mixture thereof. The solvent may be, for example, acetonitrile, dichloromethane, 1,2-dichloroethane, chloroform, DME, DMF, DMA, 1,4-dioxane, THF, diethyl ether, diisopropyl ether, benzene, toluene, xylene, pyridine, NMP, water or the like. These solvents are used alone or as a mixture thereof.

Step 4

The compound (Ia) can be prepared by reacting the compound (XV) with the compound (V) of which the amount is preferably 0.1 to 10 Eq, in a solvent or solvent-free environment, if needed in the presence of a suitable base of which the amount is preferably 1 to 10 Eq, at a temperature of 0 to 300° C. for 5 minutes to 72 hours.

The base may be, for example, potassium carbonate, sodium carbonate, potassium bicarbonate, sodium bicarbonate, potassium hydroxide, potassium hydroxide, triethylamine, diisopropylethylamine, N-methylmorpholine, pyridine, DBU or the like. The solvent may be, for example, methanol, ethanol, propanol, butanol, DMF, DMA, NMP, acetonitrile, diethyl ether, THF, DME, 1,4-dioxane, dimethyl sulfoxide (DMSO) or the like. These solvents are used alone or as a mixture thereof.

The compound (XV) can be obtained commercially, or can be obtained by the method described in the following Production Method 3 etc.

Step 5

The compound (VI) can be prepared from the compound (II) and the compound (XV) in the same manner as in the foregoing Step 4.

Step 6

The compound (VII) can be prepared from the compound (VI) in the same manner as in the foregoing Step 1.

Step 7

The compound (VII) can also be prepared from the compound (III) in the same manner as in the foregoing Step 4.

Step 8

The compound (VIII) can be prepared from the compound (VII) in the same manner as in the foregoing Step 2.

Step 9

The compound (Ia) can also be prepared from the compound (VIII) in the same manner as in the foregoing Step 3.

Step 10

The compound (IX) can be prepared by reacting the compound (II) with a cyanating agent of which the amount is preferably 1 to 10 Eq, in a solvent, in the presence of a catalyst of which the amount is preferably 1 to 100 mol % and in the presence of a catalyst ligand of which the amount is preferably 1 to 100 mol %, and if needed in the presence of a base and an additive of which each amount is preferably 1 to 10 Eq, at a temperature of 0° C. to the boiling point of the solvent to be used for 5 minutes to 72 hours.

The catalyst may be, for example, palladium acetate, tris (dibenzylidene acetone)dipalladium or a chloroform adduct thereof, tetrakis(triphenylphosphine)palladium or the like. The catalyst ligand may be, for example, tributylphosphine, 1,1'-bis(diphenylphosphino)ferrocene (DPPF) or the like. The base may be, for example, potassium carbonate, sodium carbonate, sodium bicarbonate, tetramethylethylenediamine (TMEDA), pyridine, triethylamine, diisopropylethylamine, DBU, DMAP or the like. The additive may be, for example, copper(I) iodide, potassium iodide, zinc powder, iron(III) chloride or the like. The cyanating agent may be, for example, copper(I) cyanide, sodium cyanide, potassium cyanide, tetrabutylammonium cyanide, zinc cyanide, copper(I) potassium cyanide, trimethylsilyl cyanide or the like. The solvent may be, for example, THF, DME, 1,4-dioxane, DMF, DMA, NMP, DMSO, toluene or the like. These solvents are used alone or as a mixture thereof.

Step 11

The compound (X) can be prepared from the compound (IX) in the same manner as in the foregoing Step 4.

Step 12

The compound (VIII) can be prepared by hydrolyzing the compound (X) in a solvent, in the presence of a base of which the amount is preferably 1 Eq to a large excessive amount or in the presence of an acid of which the amount is preferably a catalytic amount to a large excessive amount, at a temperature of 0° C. to the boiling point of the solvent to be used for 5 minutes to 72 hours.

The base may be, for example, sodium hydroxide, potassium hydroxide, lithium hydroxide or the like.

The acid may be, for example, hydrochloric acid, sulfuric acid, acetic acid, trifluoroacetic acid, methanesulfonic acid or the like.

The solvent may be, for example, methanol, ethanol, propanol, THF, 1,4-dioxane, DME, toluene, dichloromethane, DMF or the like. These solvents are used alone or as a mixture thereof.

Step 13

The compound (Ib) can be prepared by reacting the compound (X) with $R^4M^1$ (wherein $R^4$ and $M^1$ have the same definitions as described above) of which the amount is preferably 1 to 10 Eq, in a solvent at a temperature of −90° C. to the boiling point of the solvent to be used for 5 minutes to 72 hours, followed by hydrolysis in the presence of an excessive amount of an acid, if needed.

The acid may be, for example, hydrochloric acid, sulfuric acid or the like. The solvent may be, for example, diethyl ether, THF, 1,4-dioxane, DME, toluene, hexane or the like. These solvents are used alone or as a mixture thereof.

Step 14

The compound (XII) can be prepared from the compound (II) in accordance with the method in the description of WO 2006/040520 etc.

For example, the compound (XII) can be prepared by reaction of the compound (XI) of which the amount is 1 Eq to a large excessive amount, in a solvent or solvent-free environment, if needed in the presence of a base of which the amount is preferably 1 to 20 Eq, if needed using an airtight container such as a sealed container and if needed using a microwave reactor, in the range of room temperature to 250° C. for 5 minutes to 72 hours.

The base may be, for example, potassium carbonate, sodium carbonate, potassium bicarbonate, sodium bicarbonate, triethylamine, diisopropylethylamine, N-methylmorpholine, pyridine, DBU or the like.

The solvent may be, for example, THF, 1,2-dimethoxyethane (DME), benzene, toluene, xylene, 1,4-dioxane, DMF, DMA, NMP, water or the like. These solvents are used alone or as a mixture thereof.

Step 15

The compound (Ic) can be prepared from the compound (XII) and the compound (XV) in the same manner as in the foregoing Step 4.

Step 16

The compound (Id) can be prepared by reacting the compound (Ic) with the compound (XIII) of which the amount is preferably 1 to 20 Eq, in a solvent, if needed in the presence of a base of which the amount is preferably 1 to 20 Eq, at a temperature of −10° C. to the boiling point of the solvent to be used for 5 minutes to 72 hours.

The compound (XIII) can be obtained commercially, or can be obtained in accordance with or by reference to a known method (for example, New Lecture of Experimental Chemistry (Shin Jikken Kagaku Kouza), 4th edition, vol. 14, p. 1106, p. 1120, published by Maruzen Co., Ltd. (1977) etc.).

The base may be, for example, potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, 4-dimethylaminopyridine or the like. These bases can be used alone or as a mixture thereof. The solvent may be, for example, methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water or the like. These solvents are used alone or as a mixture thereof.

The compound (Id) in which $R^8$ is —CONHR$^{10}$ can also be prepared by reacting the compound (Ic) with the compound (XIV) of which the amount is preferably 1 to 10 Eq, in a solvent or solvent-free environment at a temperature of −30° C. to the boiling point of the solvent to be used for 5 minutes to 72 hours.

The compound (XIV) can be obtained commercially, or can be obtained in accordance with or by reference to a known method (for example, Lecture of Experimental Chemistry (Jikken Kagaku Kouza), 4th edition, vol. 20, p. 304, p. 360, published by Maruzen Co., Ltd. (1992)).

The solvent may be, for example, methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water or the like. These solvents are used alone or as a mixture thereof.

Production Method 2

Among Compounds (I), Compound (Ie) in which $R^3$ is —C(=S) NR$^5$R$^6$, and Compound (If) in which $R^3$ is —C(=S)R$^4$ can be produced according to the following step.

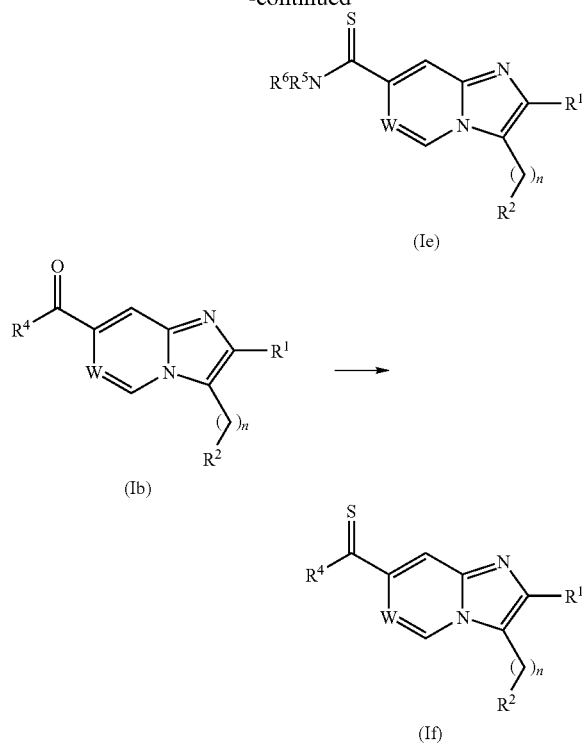

(wherein $R^1$, $R^2$, $R^4$, $R^5$, $R^6$, W and n have the same definitions as described above, respectively.)

The compound (Ie) can be prepared by reacting the compound (Ia) obtained in Production Method 1, in a solvent, with a suitable sulfurizing agent, such as diphosphorus pentasulfide and Lawesson's reagent, of which the amount is preferably 1 to 10 Eq, if needed in the presence of a base of which the amount is preferably 0.1 to 10 Eq, at a temperature of −10° C. to the boiling point of the solvent to be used for 5 minutes to 72 hours. The compound (If) can be prepared by reacting the compound (Ib) prepared in Production Method 1 in the same manner as above.

The base may be, for example, triethylamine, diisopropylethylamine, pyridine, N-methylmorpholine, DBU, potassium carbonate, sodium carbonate, potassium hydroxide, sodium hydroxide or the like. The solvent may be, for example, dichloromethane, chloroform, diethyl ether, THF, 1,4-dioxane, DME, toluene, xylene, hexane, pyridine, water or the like. These solvents are used alone or as a mixture thereof.

Production Method 3

Compound (XV) can be produced according to the following step.

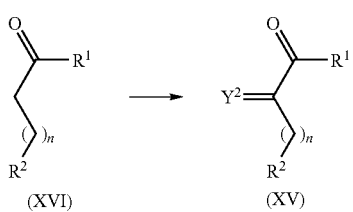

(wherein $R^1$, $R^2$, $Y^2$ and n have the same definitions as described above, respectively.)

The compound (XV) can be prepared by reacting the compound (XVI) with a halogenating agent of which the amount is 1 to 200 Eq, preferably 1 to 5 Eq, in a solvent or solvent-free environment at a temperature of −30 to 150° C. for 5 minutes to 72 hours.

The halogenating agent may be, for example, chlorine, bromine, iodine, N,N,N,N-tetra-n-butylammonium tribromide, pyridinium tribromide or the like. The solvent may be, for example, acetone, 1,4-dioxane, acetonitrile, chloroform, dichloromethane, THF, DME, ethyl acetate, DMF, acetic acid, water or the like. These solvents are used alone or as a mixture thereof.

The compound (XVI) can be obtained commercially, or can be obtained in accordance with or by reference to a known method (for example, J. Am. Chem. Soc., vol. 71, p. 4141 (1949) etc.).

Production Method 4

Among Compounds (I), Compound (Ig) in which $R^2$ is $R^{17}$, an aliphatic heterocyclic group bonded via a nitrogen atom, can be produced according to the following steps.

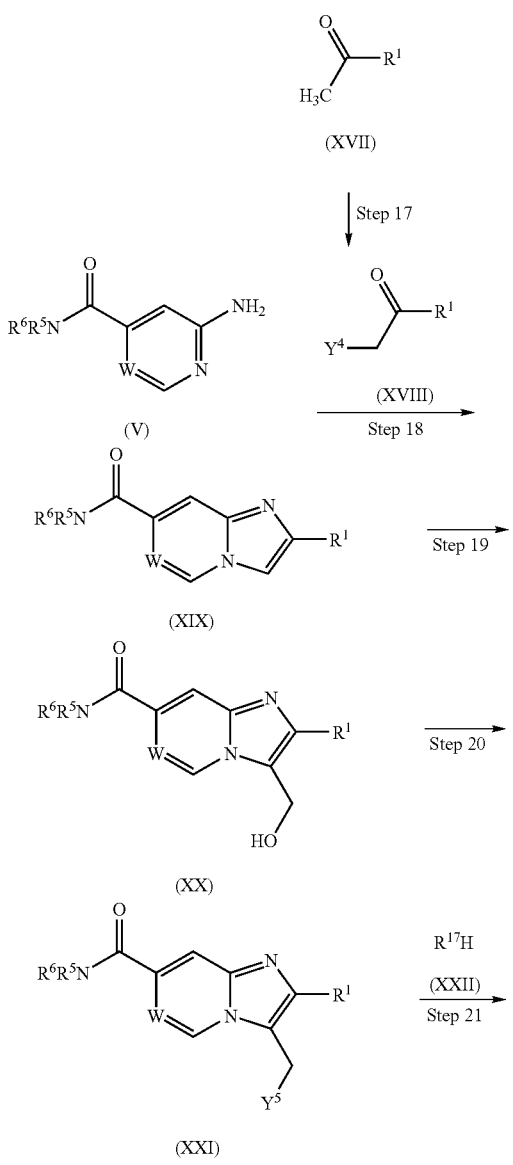

$$\underset{(Ig)}{\overset{R^6R^5N}{\underset{W}{\bigvee}}\overset{O}{\underset{N}{\bigvee}}\overset{N}{\underset{R^{17}}{\bigvee}}R^1}$$

(wherein Y$^4$ represents a chlorine atom, a bromine atom or an iodine atom; Y$^5$ represents a chlorine atom, a bromine atom, an iodine atom, methanesulfonyloxy, trifluoromethanesulfonyloxy or p-toluenesulfonyloxy; R$^{17}$ represents, among the above R$^2$, an aliphatic heterocyclic group bonded via a nitrogen atom; and R$^1$, R$^5$, R$^6$ and W have the same definitions as described above.)

Step 17

The compound (XVIII) can be prepared from the commercially available compound (XVII) in the same manner as in the foregoing Production Method 3.

Step 18

The compound (XIX) can be prepared from the compound (V) obtained in the foregoing Production Method 1 and the compound (XVIII) in the same manner as in the foregoing Step 4.

Step 19

The compound (XX) can be obtained in accordance with or by reference to a known method (for example, Lecture of Experimental Chemistry (Jikken Kagaku Kouza), 5th edition, vol. 14, p. 221, published by Maruzen Co., Ltd. (2005) etc.).

For example, the compound (XX) can be prepared by reacting the compound (XIX) with formaldehyde source of which the amount is 1 Eq to a large excessive amount, in a solvent or solvent-free environment, if needed in the presence of an additive of which the amount is a catalytic amount to 30 Eq, in the range of room temperature to the boiling point of the solvent to be used for 5 minutes to 72 hours.

The solvent may be, for example, dichloroethane, carbon tetrachloride, toluene, xylene, water or the like.

The additive may be, for example, hydrochloric acid, sulfuric acid, acetic acid, aluminum chloride, boron trifluoride ether complex or the like.

The formaldehyde source may be, for example, an aqueous formalin solution, paraformaldehyde or the like.

Step 20

The compound (XXI) can be prepared by reacting the compound (XX), in a solvent or solvent-free environment, with a halogenating agent of which the amount is preferably 1 Eq to a large excessive amount or with a sulfonylating agent of which the amount is preferably 1 to 10 Eq, and/or if needed in the presence of a base of which the amount is preferably a catalytic amount to 10 Eq, at a temperature of −20 to 150° C. for 5 minutes to 72 hours.

The halogenating agent may be, for example, phosphorus oxychloride, phosphorus oxybromide, phosphorus pentachloride, phosphorus trichloride, thionyl chloride or the like.

The sulfonylating agent may be, for example, trifluoromethanesulfonic anhydride, methanesulfonic anhydride, methanesulfonyl chloride, p-toluenesulfonyl chloride, p-toluenesulfonic anhydride or the like.

The base may be, for example, triethylamine, diisopropylethylamine, pyridine or the like.

The solvent may be, for example, dichloromethane, chloroform, 1,2-dichloroethane, toluene, ethyl acetate, acetonitrile, diethyl ether, THF, DME, dioxane, DMF, DMA, NMP, pyridine or the like. These solvents are used alone or as a mixture thereof.

Step 21

The compound (Ig) can be prepared by reacting the compound (XXI) with the compound (XXII) of which the amount is preferably 1 to 10 Eq, in a solvent or solvent-free environment, if needed in the presence of sodium iodide or potassium iodide of which the amount is preferably 1 to 10 Eq and/or if needed in the presence of a base of which the amount is preferably 1 to 10 Eq, at a temperature of −20 to 150° C. for 5 minutes to 72 hours.

The base may be, for example, potassium carbonate, potassium hydroxide, sodium hydroxide, sodium methoxide, potassium tert-butoxide, triethylamine, diisopropylethylamine, N-methylmorpholine, pyridine, DBU or the like.

The solvent may be, for example, methanol, ethanol, dichloromethane, chloroform, 1,2-dichloroethane, toluene, ethyl acetate, acetonitrile, diethyl ether, THF, DME, dioxane, DMF, DMA, NMP, pyridine, water or the like. These solvents are used alone or as a mixture thereof.

Transformation of a functional group contained in R$^1$, R$^2$ or R$^3$ of Compound (I) can also be carried out by a known method [for example, the method described in Comprehensive Organic Transformations 2nd edition, R. C. Larock, Vch Verlagsgesellschaft Mbh (1999), etc.] or a modified method thereof.

The intermediates and the desired compounds in the above-mentioned respective Production Methods can be isolated and purified through a separation and purification method generally employed in organic synthetic chemistry, for example, filtration, extraction, washing, drying, concentration, recrystallization, various types of chromatography, and the like. Further, the intermediate can be subjected to the subsequent reaction without particularly undergoing purification.

Among Compounds (I), some may include geometric isomers, stereoisomers such as optical isomers, tautomers, and the like. All possible isomers including these and mixtures thereof are included in the present invention.

To obtain a salt of Compound (I), when Compound (I) is obtained in the form of a salt, it may be purified as it is. Further, when Compound (I) is obtained in a free form, Compound (I) may be dissolved or suspended in a suitable solvent, followed by addition of an acid or a base to form a salt, and then, the resulting salt may be isolated and purified.

Further, Compounds (I) and pharmaceutically acceptable salts thereof may exist in the form of adducts with water or any of various solvents in some cases, and these adducts are also included in the present invention.

Specific examples of Compounds (I) obtained according to the invention are shown in Table 1. However, the compounds of the invention are not limited to these.

TABLE 1

(I)

| Example No. | Compound No. | R³— | W | R² | n | R¹ |
|---|---|---|---|---|---|---|
| 1 | 1 | H₃C-CH₂-N(CH₂CH₃)-C(=O)- | CH | cyclohexyl | 1 | -C(CH₃)₃ |
| 2 | 2 | H₃C-CH₂-N(CH₂CH₃)-C(=O)- | CH | tetrahydropyran-4-yl | 1 | -C(CH₃)₃ |
| 3 | 3 | H₃C-CH₂-N(CH₃)-C(=O)- | CH | tetrahydropyran-4-yl | 1 | -C(CH₃)₃ |
| 4 | 4 | H₃C-CH₂-CH₂-N(CH₂CH₃)-C(=O)- | CH | tetrahydropyran-4-yl | 1 | -C(CH₃)₃ |
| 5 | 5 | F₃C-CH₂-N(CH₂CF₃)-C(=O)- | CH | tetrahydropyran-4-yl | 1 | -C(CH₃)₃ |
| 6 | 6 | pyrrolidin-1-yl-C(=O)- | CH | tetrahydropyran-4-yl | 1 | -C(CH₃)₃ |
| 7 | 7 | piperidin-1-yl-C(=O)- | CH | tetrahydropyran-4-yl | 1 | -C(CH₃)₃ |
| 8 | 8 | H₃C-CH₂-N(CH₂CH₃)-C(=S)- | CH | tetrahydropyran-4-yl | 1 | -C(CH₃)₃ |

TABLE 1-continued (I)

| Example No. | Compound No. | R³— | W | R² | n | R¹ |
|---|---|---|---|---|---|---|
| 9 | 9 | phenyl-C(=O)- | CH | tetrahydropyran-4-yl | 1 | -C(CH₃)₃ |
| 10 | 10 | H₃C-CH₂-C(=O)- | CH | tetrahydropyran-4-yl | 1 | -C(CH₃)₃ |
| 11 | 11 | (H₃C-CH₂)₂N-C(=O)- | CH | phenyl | 1 | -C(CH₃)₃ |
| 12 | 12 | (H₃C-CH₂)₂N-C(=O)- | CH | cyclohexyl | 2 | -C(CH₃)₃ |
| 13 | 13 | (H₃C-CH₂)₂N-C(=O)- | CH | tetrahydropyran-4-yl | 2 | -C(CH₃)₃ |
| 14 | 14 | (H₃C-CH₂)₂N-C(=O)- | N | cyclohexyl | 1 | -C(CH₃)₃ |
| 15 | 15 | (H₃C-CH₂)₂N-C(=O)- | N | tetrahydropyran-4-yl | 1 | -C(CH₃)₃ |
| 16 | 16 | (H₃C-CH₂)₂N-C(=S)- | N | tetrahydropyran-4-yl | 1 | -C(CH₃)₃ |

TABLE 1-continued
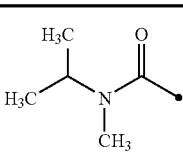
(I)
| Example No. | Compound No. | R³— | W | R² | n | R¹ |
|---|---|---|---|---|---|---|
| 17 | 17 | 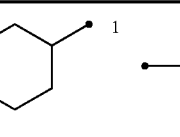 | CH | 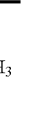 | 1 | 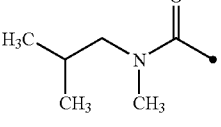 |
| 18 | 18 | 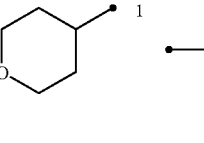 | CH |  | 1 | 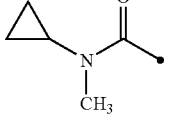 |
| 19 | 19 | 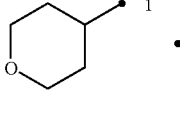 | CH |  | 1 | 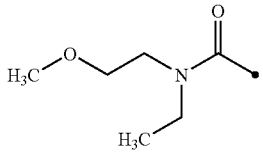 |
| 20 | 20 | 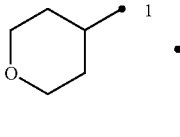 | CH |  | 1 | 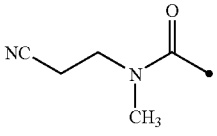 |
| 21 | 21 | 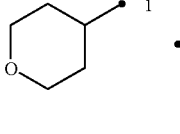 | CH | 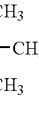 | 1 | 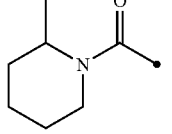 |
| 22 | 22 | 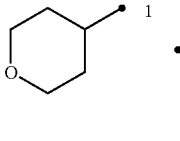 | CH | 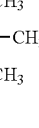 | 1 | 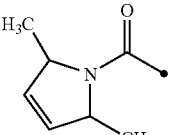 |
| 23 | 23 | 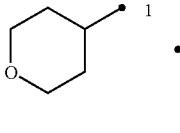 | CH |  | 1 | 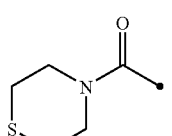 |
| 24 | 24 | 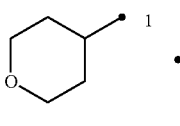 | CH | 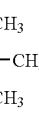 | 1 | |

TABLE 1-continued
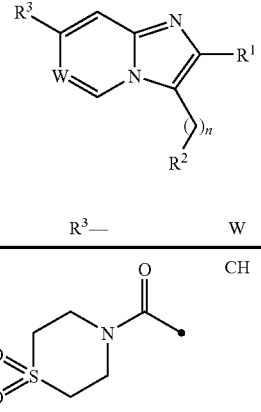
(I)
| Example No. | Compound No. | R³— | W | R² | n | R¹ |
|---|---|---|---|---|---|---|
| 25 | 25 | 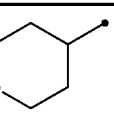 | CH | 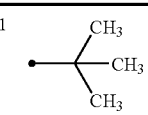 | 1 | 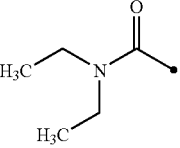 |
| 26 | 26 | 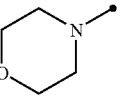 | CH | 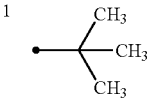 | 1 | 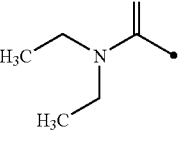 |
| 27 | 27 | 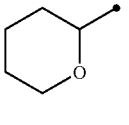 | CH | 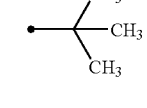 | 1 | 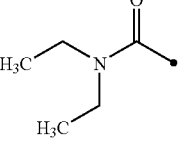 |
| 28 | 28 | 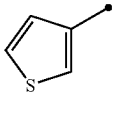 | CH | 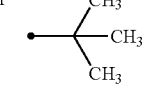 | 1 |  |
| 29 | 29 | 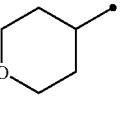 | CH | 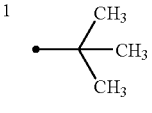 | 1 | 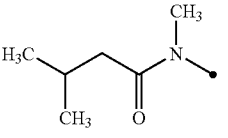 |
| 30 | 30 | 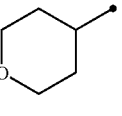 | CH | 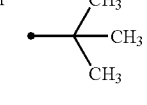 | 1 | 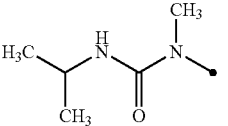 |
| 31 | 31 | 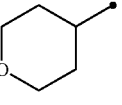 | CH | 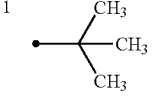 | 1 | 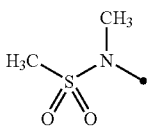 |
| 32 | 32 | 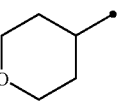 | CH | 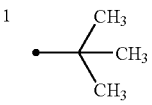 | 1 | 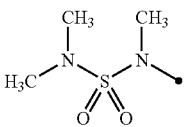 |
| 33 | 33 | 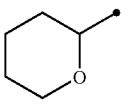 | CH | 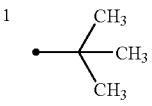 | 1 | |

Subsequently, pharmacological activities of some typical Compounds (I) will be specifically described with reference to Test examples.

TEST EXAMPLE 1

Cannabinoid CB1 and CB2 receptor-binding activities ([$^3$H]CP55940 binding assay)

The assay was performed according to a method of Hillard et al. (The Journal of Pharmacology and Experimental Therapeutics, vol. 289, p. 1427 (1999)). A rat forebrain membrane sample was prepared for use in the binding assay for CB1 receptor, and a rat spleen membrane sample was prepared for use in the binding assay for CB2 receptor. Each membrane sample (forebrain: final concentration of 0.5 mg·protein/mL, spleen: final concentration of 2 mg·protein/mL) together with each test compound and [$^3$H]CP55940 ((−)-cis-3-[2-hydroxy-[3,5-$^3$H]-4-(1,1-dimethylheptyl)-phenyl]-trans-4-(3-hydroxypropyl)cyclohexanol, manufactured by PerkinElmer, final concentration of 0.5 nmol/L), was incubated at 25° C. for 1 hour in the assay buffer solution (50 mmol/L Tris-HCl buffer solution (pH 7.4), 1 mmol/L EDTA and 3 mmol/L MgCl$_2$) containing 0.1% bovine serum albumin. Then, the mixture was filtered through a glass filter GF/C (manufactured by Whatman) pretreated with 1% polyethyleneimine. After the glass filter was washed with the assay buffer solution containing 0.2% bovine serum albumin, the radioactivity on the glass filter was measured using a liquid scintillation counter (TRI-CARB 2700TR, manufactured by Packard). The nonspecific binding amount was defined as a binding amount in the presence of 10 μmol/L WIN-55215-2 ((R)-(+)-[2,3-dihydro-5-methyl-3-(4-morpholinylmethyl)-pyrrolo[1,2,3-de]-1,4-benzoxazin-6-yl]-1-naphthalenyl-methanone, manufactured by Tocris). The specific binding amount was presented as the difference between the total binding amount and the nonspecific binding amount. The 50% inhibitory concentration (IC$_{50}$ value) of the test compound in the specific binding was determined. The Ki value of the test compound was calculated from this IC$_{50}$ value and the Kd value for [$^3$H]CP55940 binding.

As a result, the Ki value of each of Compounds 1, 2, 8, 14, 15, 16, 17, 18 and 27 for CB2 receptor was <1 μmol/L. It was shown that the compound (I) or the pharmaceutically acceptable salt thereof has an affinity to CB2 receptor. Further, the Ki value of the compound (I) or the pharmaceutically acceptable salt thereof for CB2 receptor was smaller than its Ki value for CB1 receptor. That is, the compound (I) or the pharmaceutically acceptable salt thereof showed a selective affinity to CB2 receptor.

TEST EXAMPLE 2

GTPγS binding assay via human CB2 receptor

The assay was performed according to a method of Hillard et al. (The Journal of Pharmacology and Experimental Therapeutics, vol. 289, p. 1427 (1999)). For use as a membrane sample, a membrane fraction was prepared from human CB2 receptor stably expressing CHO-K1 cells (Nature, vol. 365, pp. 61-65 (1993)). The membrane sample (final concentration of 40 μg·protein/mL) together with each test compound and [$^{35}$S]GTPγS (manufactured by PerkinElmer, final concentration of 0.05 nmol/L), was incubated at 30° C. for 1 hour in the assay buffer solution (50 mmol/L Tris-HCl buffer solution (pH 7.4), 100 mmol/L NaCl, 1 mmol/L EDTA, 3 mmol/L MgCl$_2$ and 0.1% bovine serum albumin) containing 20 μmol/L guanosine 5'-diphosphate (GDP). Then, the mixture was filtered through a glass filter GF/B (manufactured by Whatman). After the glass filter was washed with the assay buffer solution, the radioactivity on the glass filter was measured using a liquid scintillation counter (TRI-CARB 2700TR, manufactured by Packard). The nonspecific binding amount was defined as a binding amount in the presence of 10 μmol/L GTPγS. The specific binding amount was presented as the difference between the total binding amount and the nonspecific binding amount. The increase rate of the specific binding amount in the presence of the test compound relative to the specific binding amount in the absence of the test compound was defined as agonist activity of the test compound. The concentration which gives 50% of the maximum effect of the test compound (EC$_{50}$ value) was calculated by nonlinear regression analysis of the concentration-response curve. The percentage of the maximum effect of the test compound (E$_{max}$ value) was calculated based on the maximum effect of CP55940 (manufactured by Tocris) measured simultaneously set to 100%.

The EC$_{50}$ value of each of Compounds 1, 2, 8, 14, 15, 16, 17 and 18 was <1 μmol/L, and the E$_{max}$ value thereof was >30%. This result showed that each of these compounds has agonist activity to CB2 receptor. That is, this result suggests that the compound (I) or the pharmaceutically acceptable salt thereof has agonist activity to CB2 receptor.

From the above results, it was shown that Compound (I) or a pharmaceutically acceptable salt thereof has a high affinity for the CB2 receptor and is useful as a CB2 receptor agonist. Accordingly, it was considered that Compound (I) or a pharmaceutically acceptable salt thereof is useful as a therapeutic and/or preventive agent for a disease associated with a CB2 receptor.

It has been well known that CB2 receptor agonists are effective as anti-inflammatory agents [Nature, vol. 365, p. 61 (1993); British Journal of Pharmacology, vol. 139, p. 775 (2003)] or therapeutic agents for diseases such as a pain [Pain, vol. 93, p. 239 (2001); Proceedings of the National Academy of Science of the United States of America, vol. 102, p. 3093 (2005); European Journal of Neuroscience, vol. 17, p. 2750 (2003); European Journal of Neuroscience, vol. 22, p. 371 (2005); European Journal of Neuroscience, vol. 23, p. 1530 (2006)], pruritus (WO2002/065997; WO2003/035109; WO2003/070277; WO2006/046778), or osteoporosis [Proceedings of the National Academy of Science of the United States of America, vol. 103, p. 696 (2006)]. Accordingly, it was considered that Compound (I) or a pharmaceutically acceptable salt thereof is useful as a therapeutic and/or preventive agent for pains (such as neuropathic pain, trigeminal neuralgia, diabetic pain, postherpetic neuralgia, neuropathic low back pain, HIV-related pain, fibromyalgia, cancer pain, inflammatory pain, acute pain, chronic pain, postoperative pain, acute pain after tooth extraction, chronic musculoskeletal pain, noxious pain, psychogenic pain, and menstrual pain), migraine, pruritus, inflammation, allergies, immunodeficiency, autoimmune diseases, chronic rheumatoid arthritis, osteoarthritis, inflammatory bowel disease, irritable bowel syndrome, multiple sclerosis, asthma (such as airway inflammatory cell infiltration, airway hyperresponsiveness, bronchoconstriction, and mucus hypersecretion), chronic obstructive lung disease, emphysema, pulmonary fibrosis, coughing, allergic rhinitis, dermatitis, atopic dermatitis, arteriosclerosis, glaucoma, anorexia, osteoporosis, or the like.

TEST EXAMPLE 3

Analgesic Effect of Compounds in Rats with Chronic Constriction Nerve Injury

Rats with chronic constriction nerve injury were produced by partially modifying the method of Mosconi and Kruger et al. (Pain, vol. 64, pp. 37-57 (1996)).

Male Crl:CD(SD) rats were used for the experiments. Under pentobarbital anesthesia, the sciatic nerve of the left hind limb of the rat was exfoliated, and the exfoliated region was wrapped with a polyethylene tube (trade name: Intramedic, size: PE-60, manufactured by Becton Dickinson and Company) of 2 mm in length. On days 14 to 21 after the surgery, the rats were placed in an acrylic connected cage with a wire mesh floor (900 mm (length)×210 mm (depth)×140 mm (height)) consisting of 4 cages connected in a row and allowed to acclimate to the environment for at least 20 minutes, and then, the pain was evaluated.

The von Frey filament (trade name: touch test sensory evaluator, Model number: model 58011, manufactured by Muromachi Kikai) was used to evaluate pain, and the results were calculated as a pain threshold. That is, by using a von Frey filament of different stimulus intensity, stimulation was given to the plantar surface of the injured side of rats with chronic constriction nerve injury, and the stimulus intensity to cause paw withdrawal response was obtained. Then, the 50% pain threshold (Paw withdrawal threshold) (g) was calculated by the up down method of Dixon [Annual Review of Pharmacology and Toxicology, vol. 20, pp. 441-462 (1980)]. Incidentally, a normal rat exhibited the 50% pain threshold of from 10 to 12 g on an average.

In the evaluation of the test compound, rats with 50% pain threshold of less than 4 g were used, and the test compound was dissolved in a 0.5% aqueous methyl cellulose solution and orally administered at a dose of 5 mL/kg. One hour after the administration, the pain threshold was measured using von Frey filaments.

As the results, Compounds 2, 15, 17 and 18 significantly increased the pain threshold at a dose of 50 mg/kg or less. That is, it was confirmed that these compounds have a preventive and/or therapeutic effect on pain.

Accordingly, it was confirmed that Compound (I) or a pharmaceutically acceptable salt thereof is useful as a therapeutic and/or preventive agent for a pain, and is useful as a therapeutic and/or preventive agent for pains such as neuropathic pain, trigeminal neuralgia, diabetic pain, postherpetic neuralgia, neuropathic low back pain, HIV-related pain, fibromyalgia, cancer pain, or inflammatory pain.

Compound (I) or a pharmaceutically acceptable salt thereof can be administered alone as it is. However, usually, Compound (I) or a pharmaceutically acceptable salt thereof is preferably provided as various pharmaceutical preparations. Further, such pharmaceutical preparations are to be used in animals or humans.

The pharmaceutical preparations according to the present invention can contain Compound (I) or a pharmaceutically acceptable salt thereof alone as an active ingredient or a mixture thereof with an optional active ingredient for any other treatment. Further, these pharmaceutical preparations are prepared by mixing the active ingredient with one or more pharmaceutically acceptable carriers (such as a diluent, a solvent and an excipient) and then subjecting the mixture to any method well known in the technical field of pharmaceutics.

As for the administration route, it is preferred to select the most effective route of administration in the treatment. Examples of the administration route include an oral administration and a parenteral administration such as an intravenous administration.

As for the dosage form, for example, tablets, injections, and the like are included.

For example, the tablet suitable for oral administration can be prepared with an excipient such as lactose, a disintegrator such as starch, a lubricant such as magnesium stearate, a binder such as hydroxypropyl cellulose, or the like.

For example, the injection suitable for parenteral administration can be prepared with a diluent or a solvent such as a brine solution, a glucose solution, or a mixture of brine and a glucose solution, or the like.

The doses and the frequencies of administration of Compound (I) or a pharmaceutically acceptable salt thereof may vary depending on dosage form, age and body weight of a patient, nature or seriousness of the symptom to be treated, and the like. However, in the oral administration, in general, a dose of 0.01 to 1000 mg, preferably, 0.05 to 100 mg is administered to an adult patient once or several times a day. In the parenteral administration such as intravenous administration, a dose of 0.001 to 1000 mg, preferably, 0.01 to 100 mg is administered to an adult patient once or several times a day. However, these doses and frequencies of administration vary depending on the various conditions described above.

Hereinafter, the invention will be described more specifically with reference to Examples and Reference Examples, however, the scope of the invention is not limited to these examples.

A proton nuclear magnetic resonance spectrum ($^1$H-NMR) used in Examples and Reference Examples was measured at 270 MHz or 300 MHz, and exchangeable proton may not be clearly observed in some cases depending on the compounds and measurement conditions. Further, for the descriptions of the multiplicity of signals, those generally applied are used, and the symbol "br" represents an apparent broad signal.

EXAMPLE 1

2-tert-Butyl-3-cyclohexylmethyl-N,N-diethylimidazo[1,2-a]-pyridine-7-carboxamide (Compound 1)

2-tert-Butyl-3-cyclohexylmethylimidazo[1,2-a]pyridine-7-carboxylic acid (82.0 mg, 0.260 mmol) obtained in Reference Example 3 was dissolved in DMF (1.0 mL). To this were added diethylamine (53.0 μL, 0.290 mmol), 1-(3-dimethylaminopropyl)-3-ethylcarbodiimide hydrochloride (101 mg, 0.510 mmol) and 1-hydroxybenzotriazole hydrate (86.0 mg, 0.560 mmol). Then, the mixture was stirred at room temperature for 2 hours. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by column chromatography on silica gel (hexane/ethyl acetate=70/30), and the resulting crude crystals were reslurried with hexane to give the title compound 1 (83.0 mg, 0.220 mmol, yield 84%).

$^1$H-NMR (δ ppm, CDCl$_3$): 7.88 (dd, J=7.1, 0.8 Hz, 1H), 7.55-7.50 (m, 1H), 6.80 (dd, J=7.1, 1.7 Hz, 1H), 3.48 (q, J=7.0 Hz, 4H), 2.91 (d, J=7.1 Hz, 2H), 1.75-1.64 (m, 6H), 1.48 (s, 9H), 1.23-1.07 (m, 11H). Mass (m/z): ESIMS m/z: 370 [M+H]$^+$.

EXAMPLE 2

2-tert-Butyl-N,N-diethyl-3-(tetrahydropyran-4-ylmethyl)-imidazo[1,2-a]pyridine-7-carboxamide (Compound 2)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid, the same procedure as described in Example 1 was performed to give the title compound 2 (54.0 mg, 0.150 mmol, yield 70%).

$^1$H-NMR (δ ppm, CDCl$_3$): 7.89 (d, J=7.0 Hz, 1H), 7.54 (s, 1H), 6.83 (dd, J=7.0, 1.5 Hz, 1H), 4.00-3.92 (m, 2H), 3.48 (q, J=7.0 Hz, 4H), 3.34-3.26 (m, 2H), 2.99 (d, J=7.1 Hz, 2H), 1.99-1.90 (m, 1H), 1.54-1.47 (m, 4H), 1.48 (s, 9H), 1.21 (t, J=7.0 Hz, 6H). ESIMS m/z: 372 [M+H]$^+$.

EXAMPLE 3

2-tert-Butyl-N-ethyl-N-methyl-3-(tetrahydropyran-4-ylmethyl)imidazo[1,2-a]pyridine-7-carboxamide (Compound 3)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that ethylmethylamine was used instead of diethylamine, the same procedure as described in Example 1 was performed to give the title compound 3 (49.0 mg, 0.140 mmol, yield 60%).

$^1$H-NMR (δ ppm, CDCl$_3$): 7.89 (dd, J=7.1, 0.7 Hz, 1H), 7.56 (dd, J=1.7, 0.7 Hz, 1H), 6.87 (dd, J=7.1, 1.7 Hz, 1H), 4.00-3.90 (m, 2H), 3.50 (q, J=7.1 Hz, 2H), 3.37-3.23 (m, 2H), 3.07 (s, 3H), 3.00 (d, J=7.4 Hz, 2H), 2.01-1.89 (m, 1H), 1.54-1.48 (m, 4H), 1.48 (s, 9H), 1.21 (t, J=7.1 Hz, 3H). ESIMS m/z: [M+H]$^+$ 358.

EXAMPLE 4

2-tert-Butyl-N-ethyl-N-propyl-3-(tetrahydropyran-4-ylmethyl)imidazo[1,2-a]pyridine-7-carboxamide (Compound 4)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that ethylpropylamine was used instead of diethylamine, the same procedure as described in Example 1 was performed to give the title compound 4 (58.0 mg, 0.150 mmol, yield 95%).

$^1$H-NMR (δ ppm, CDCl$_3$): 7.89 (dd, J=7.0, 0.8 Hz, 1H), 7.54 (dd, J=1.7, 0.8 Hz, 1H), 6.83 (dd, J=7.0, 1.7 Hz, 1H), 4.00-3.93 (m, 2H), 3.52-3.23 (m, 6H), 2.99 (d, J=7.3 Hz, 2H), 2.02-1.89 (m, 1H), 1.70-1.60 (m, 2H), 1.55-1.44 (m, 4H), 1.48 (s, 9H), 1.21 (t, J=6.9 Hz, 3H), 0.89 (t, J=6.9 Hz, 3H). ESIMS m/z: [M+H]$^+$ 386.

EXAMPLE 5

2-tert-Butyl-3-(tetrahydropyran-4-ylmethyl)-N,N-bis(2,2,2-trifluoroethyl)imidazo[1,2-a]pyridine-7-carboxamide (Compound 5)

2-tert-Butyl-3-(tetrahydropyran-4-ylmethyl)imidazo-[1,2-a]pyridine-7-carboxylic acid (64.0 mg, 0.200 mmol) obtained in Reference Example 7 was dissolved in thionyl chloride (2.0 mL), and then the mixture was stirred under ref lux for 1 hour. After thionyl chloride was evaporated off in vacuo, the resulting residue was dissolved in dichloromethane (2.0 mL) To this were added diisopropylethylamine (53.0 iL, 0.300 mmol) and bis(2,2,2-trifluoroethyl) amine (67.0 iL, 0.400 mmol). Then, the mixture was stirred at room temperature overnight. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by preparative thin layer chromatography (chloroform/methanol=90/10) to give the title compound 5 (74.0 mg, 0.150 mmol, yield 76%).

$^1$H-NMR (δ ppm, CDCl$_3$): 7.97 (d, J=7.0 Hz, 1H), 7.65 (s, 1H), 6.86 (d, J=7.0 Hz, 1H), 4.30 (q, J=8.3 Hz, 4H), 4.00-3.92 (m, 2H), 3.38-3.25 (m, 2H), 3.02 (d, J=7.3 Hz, 2H), 2.02-1.88 (m, 1H), 1.59-1.40 (m, 4H), 1.49 (s, 9H). ESIMS m/z: 480 [M+H]$^+$.

EXAMPLE 6

1-[2-tert-Butyl-3-(tetrahydropyran-4-ylmethyl)imidazo-[1,2-a]pyridine-7-carbonyl]pyrrolidine (Compound 6)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that pyrrolidine was used instead of diethylamine, the same procedure as described in Example 1 was performed to give the title compound 6 (90.0 mg, 0.240 mmol, yield 77%).

$^1$H-NMR (δ ppm, CDCl$_3$): 7.88 (d, J=7.3 Hz, 1H), 7.70-7.68 (m, 1H), 7.04 (dd, J=7.3, 1.5 Hz, 1H), 4.00-3.90 (m, 2H), 3.63 (br, 4H), 3.35-3.25 (m, 2H), 3.00 (d, J=7.4 Hz, 2H), 1.93 (m, 5H), 1.55-1.44 (m, 4H), 1.49 (s, 9H). ESIMS m/z: [M+H]$^+$ 370.

EXAMPLE 7

1-[2-tert-Butyl-3-(tetrahydropyran-4-ylmethyl)imidazo-[1,2-a]pyridine-7-carbonyl]piperidine (Compound 7)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that piperidine was used instead of diethylamine, the same procedure as described in Example 1 was performed to give the title compound 7 (101 mg, 0.270 mmol, yield 83%).

$^1$H-NMR (δ ppm, CDCl$_3$): 7.89 (d, J=6.9 Hz, 1H), 7.57-7.54 (m, 1H), 6.86 (dd, J=6.9, 1.5 Hz, 1H), 4.00-3.90 (m, 2H), 3.59 (br, 4H), 3.35-3.25 (m, 2H), 2.99 (d, J=7.3 Hz, 2H), 2.00-1.90 (m, 1H), 1.75-1.40 (m, 10H), 1.48 (s, 9H). ESIMS m/z: 384 [M+H]$^+$.

EXAMPLE 8

2-tert-Butyl-N,N-diethyl-3-(tetrahydropyran-4-ylmethyl)-imidazo[1,2-a]pyridine-7-carbothioamide (Compound 8)

Compound 2 (60.0 mg, 0.160 mmol) obtained in Example 2 was dissolved in DME (1.0 mL). To this was added Lawesson's reagent (71.0 mg, 0.170 mmol), and then the mixture was stirred under ref lux for 1 hour. The solvent was evaporated off in vacuo and the residue was purified by column chromatography (hexane/ethyl acetate=50/50). The resulting crude crystals were reslurried with hexane to give the title compound (40.0 mg, 0.100 mmol, yield 65%).

$^1$H-NMR (δ ppm, CDCl$_3$): 7.82 (d, J=7.1 Hz, 1H), 7.34-7.31 (m, 1H), 6.77 (dd, J=7.1, 1.5 Hz, 1H), 4.17-4.08 (m, 2H), 4.00-3.91 (m, 2H), 3.61 (br, 2H), 3.37-3.25 (m, 2H), 2.97 (d, J=7.3 Hz, 2H), 2.02-1.85 (m, 1H), 1.61-1.47 (m, 4H), 1.47 (s, 9H), 1.45-1.15 (m, 6H). ESIMS m/z: 388 [M+H]+.

EXAMPLE 9

[2-tert-Butyl-3-(tetrahydropyran-4-ylmethyl)imidazo[1,2-a]-pyridin-7-yl]phenyl ketone (Compound 9)

2-tert-Butyl-3-(tetrahydropyran-4-ylmethyl)imidazo-[1,2-a]pyridine-7-carbonitrile (80.0 mg, 0.270 mmol) obtained in Reference Example 6 was dissolved in THF (1.0 mL). To this was slowly added a solution of phenylmagnesium bromide in THF (680 µL, 1.36 mmol) at 0° C. After the mixture was stirred at 40° C. for 1 hour, it was cooled down to 0° C. To this was added 3 mol/L hydrochloric acid (1.0 mL), and then the mixture was stirred at room temperature for 10 minutes. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by column chromatography on silica gel (hexane/ethyl acetate=70/30), and the resulting crude crystals were recrystallized from ethanol-water to give the title compound 9 (55.0 mg, 0.150 mmol, yield 52%).

$^1$H-NMR (δ ppm, CDCl$_3$): 8.00-7.95 (m, 2H), 7.82-7.78 (m, 2H), 7.62-7.38 (m, 4H), 4.41-3.92 (m, 2H), 3.36-3.26 (m, 2H), 3.04 (d, J=7.3 Hz, 2H), 2.03-1.92 (m, 1H), 1.59-1.47 (m, 4H), 1.49 (s, 9H). ESIMS m/z: 377 [M+H]+.

EXAMPLE 10

[2-tert-Butyl-3-(tetrahydropyran-4-ylmethyl)imidazo[1,2-a]-pyridin-7-yl]ethyl ketone (Compound 10)

Except that a solution of ethylmagnesium bromide in THF was used instead of the solution of phenylmagnesium bromide in THF, the same procedure as described in Example 9 was performed to give the title compound 10 (15.0 mg, 0.045 mmol, yield 17%).

$^1$H-NMR (δ ppm, CDCl$_3$): 8.25-8.21 (m, 1H), 7.91 (d, J=7.3 Hz, 1H), 7.40 (dd, J=7.3, 1.7 Hz, 1H), 4.01-3.94 (m, 2H), 3.38-3.23 (m, 2H), 3.01 (d, J=7.3 Hz, 2H), 3.01 (q, J=7.3 Hz, 2H), 2.05-1.89 (m, 1H), 1.57-1.48 (m, 4H), 1.50 (s, 9H), 1.25 (t, J=7.3 Hz, 3H). ESIMS m/z: 329 [M+H]+.

EXAMPLE 11

3-Benzyl-2-tert-butyl-N,N-diethyl-imidazo[1,2-a]pyridine-7-carboxamide (Compound 11)

Except that 2-bromo-4,4-dimethyl-1-phenylpentan-3-one obtained by a method described in Journal of Heterocyclic Chemistry, vol. 21, p. 1509 (1987) was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the title compound 11 (42.0 mg, 0.110 mmol, yield 39%).

$^1$H-NMR (δ ppm, CDCl$_3$): 7.63-7.58 (m, 2H), 7.29-7.17 (m, 3H), 7.04-6.99 (m, 2H), 6.72-6.66 (m, 1H), 4.48 (s, 2H), 3.45 (q, J=7.1 Hz, 4H), 1.50 (s, 9H), 1.19 (t, J=7.1 Hz, 6H). ESIMS m/z: 364 [M+H]+.

EXAMPLE 12

2-tert-Butyl-3-(2-cyclohexylethyl)-N,N-diethyl-imidazo-[1,2-a]pyridine-7-carboxamide (Compound 12)

Except that 4-bromo-6-cyclohexyl-2,2-dimethylhexan-3-one obtained in Reference Example 15 was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the title compound (85.1 mg, 0.222 mmol, yield 64%).

$^1$H-NMR (δ ppm, CDCl$_3$): 7.82 (d, J=6.9 Hz, 1H), 7.55 (d, J=1.6 Hz, 1H), 6.84 (dd, J=6.9, 1.6 Hz, 1H), 3.47 (q, J=7.0 Hz, 4H), 3.05-2.97 (m, 2H), 1.89-1.65 (m, 5H), 1.47 (s, 9H), 1.50-1.00 (m, 14H). ESIMS m/z: 384 [M+H]+.

EXAMPLE 13

2-tert-Butyl-N,N-diethyl-3-[2-(tetrahydropyran-4-yl)ethyl]-imidazo[1,2-a]pyridine-7-carboxamide (Compound 13)

Except that 4-bromo-2,2-dimethyl-6-(tetrahydropyran-4-yl)hexan-3-one obtained in Reference Example 20 was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the title compound (88.5 mg, 0.230 mmol, yield 67%).

$^1$H-NMR (δ ppm, CDCl$_3$): 7.81 (d, J=6.9 Hz, 1H), 7.55 (s, 1H), 6.84 (d, J=6.9 Hz, 1H), 4.05-3.96 (m, 2H), 3.54-3.37 (m, 6H), 3.07-2.99 (m, 2H), 1.75-1.37 (m, 7H), 1.47 (s, 9H), 1.20 (t, J=7.1 Hz, 6H). ESIMS m/z: 386 [M+H]+.

EXAMPLE 14

2-tert-Butyl-3-cyclohexylmethyl-N,N-diethyl-imidazo[1,2-c]-pyrimidine-7-carboxamide (Compound 14)

Except that 2-tert-butyl-3-cyclohexylmethylimidazo[1,2-c]pyrimidine-7-carboxylic acid obtained in Reference Example 11 was used instead of 2-tert-butyl-3-cyclohexylmethylimidazo[1,2-a]pyridine-7-carboxylic acid, the same procedure as described in Example 1 was performed to give the title compound 14 (55.0 mg, 0.150 mmol, yield 93%).

$^1$H-NMR (δ ppm, CDCl$_3$): 8.75 (d, J=1.0 Hz, 1H), 7.71 (d, J=1.0 Hz, 1H), 3.52 (q, J=6.9 Hz, 4H), 2.98 (d, J=7.1 Hz, 2H), 1.80-1.65 (m, 6H), 1.47 (s, 9H), 1.26-1.15 (m, 5H), 1.23 (t, J=7.1 Hz, 6H). ESIMS m/z: 371 [M+H]+.

EXAMPLE 15

2-tert-Butyl-N,N-diethyl-3-(tetrahydropyran-4-ylmethyl)-imidazo[1,2-c]pyrimidine-7-carboxamide (Compound 15)

Except that 2-tert-butyl-3-(tetrahydropyran-4-ylmethyl)imidazo[1,2-c]-pyrimidine-7-carboxylic acid obtained in Reference Example 13 was used instead of 2-tert-butyl-3-cyclohexylmethylimidazo[1,2-a]pyridine-7-carboxylic acid, the same procedure as described in Example 1 was performed to give the title compound 15 (53.0 mg, 0.140 mmol, yield 68%).

$^1$H-NMR (δ ppm, CDCl$_3$): 8.79-8.74 (m, 1H), 7.73-7.71 (m, 1H), 4.01-3.92 (m, 2H), 3.52 (q, J=7.1 Hz, 4H), 3.36-3.25 (m, 2H), 3.06 (d, J=7.3 Hz, 2H), 2.02-1.89 (m, 1H), 1.56-1.47 (m, 4H), 1.48 (s, 9H), 1.24 (t, J=7.1 Hz, 6H). ESIMS m/z: 373 [M+H]$^+$.

EXAMPLE 16

2-tert-Butyl-N,N-diethyl-3-(tetrahydropyran-4-ylmethyl)-imidazo[1,2-c]pyrimidine-7-carbothioamide (Compound 16)

Except that Compound 15 obtained in Example 15 was used instead of Compound 2, the same procedure as described in Example 8 was performed to give the title compound 16 (51.0 mg, 0.130 mmol, yield 81%).
$^1$H-NMR (δ ppm, CDCl$_3$): 8.72 (d, J=1.3 Hz, 1H), 7.57 (d, J=1.3 Hz, 1H), 4.13 (q, J=7.1 Hz, 2H), 4.02-3.93 (m, 2H), 3.55 (q, J=7.1 Hz, 2H), 3.37-3.26 (m, 2H), 3.04 (d, J=7.3 Hz, 2H), 2.02-1.87 (m, 1H), 1.53-1.47 (m, 4H), 1.47 (s, 9H), 1.41 (t, J=7.1 Hz, 3H), 1.25 (t, J=7.1 Hz, 3H). ESIMS m/z: 389 [M+H]$^+$.

EXAMPLE 17

2-tert-Butyl-N-isopropyl-N-methyl-3-(tetrahydropyran-4-ylmethyl)-imidazo[1,2-a]pyridine-7-carboxamide (Compound 17)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that N-methylisopropylamine was used instead of diethylamine, the same procedure as described in Example 1 was performed to give the title compound 17 (102 mg, 0.275 mmol, yield 87%).
$^1$H-NMR (δ ppm, CDCl$_3$): 7.89 (d, J=7.1 Hz, 1H), 7.55-7.53 (m, 1H), 6.84 (dd, J=7.1, 1.4 Hz, 1H), 4.69-4.30 (m, 1H), 4.00-3.92 (m, 2H), 3.36-3.25 (m, 2H), 3.00 (d, J=7.4 Hz, 2H), 2.93 (s, 3H), 2.02-1.87 (m, 1H), 1.55-1.47 (m, 4H), 1.49 (s, 9H), 1.20 (d, J=6.6 Hz, 6H). ESIMS m/z: 372 [M+H]$^+$.

EXAMPLE 18

2-tert-Butyl-N-isobutyl-N-methyl-3-(tetrahydropyran-4-ylmethyl)imidazo[1,2-a]pyridine-7-carboxamide (Compound 18)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that N-methylisobutylamine was used instead of diethylamine, the same procedure as described in Example 1 was performed to give the title compound 18 (94.0 mg, 0.244 mmol, yield 77%).
$^1$H-NMR (δ ppm, CDCl$_3$): 7.89 (d, J=6.9 Hz, 1H), 7.57 (s, 1H), 6.87 (d, J=6.9 Hz, 1H), 4.00-3.92 (m, 2H), 3.39-3.22 (m, 4H), 3.07 (s, 3H), 3.00 (d, J=7.4 Hz, 2H), 2.10-1.87 (m, 2H), 1.56-1.46 (m, 4H), 1.51 (s, 9H), 0.90 (brs, 6H). ESIMS m/z: 386 [M+H]$^+$.

EXAMPLE 19

2-tert-Butyl-N-cyclopropyl-N-methyl-3-(tetrahydropyran-4-ylmethyl)imidazo[1,2-a]pyridine-7-carboxamide (Compound 19)

Step 1
Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that cyclopropylamine was used instead of diethylamine, the same procedure as described in Example 1 was performed to give 2-tert-butyl-N-cyclopropyl-3-(tetrahydropyran-4-ylmethyl)-imidazo[1,2-a]pyridine-7-carboxamide (188 mg, 0.529 mmol, yield 84%).
$^1$H-NMR (δ ppm, CDCl$_3$): 7.89 (d, J=7.3 Hz, 1H), 7.81 (s, 1H), 7.26-7.22 (m, 1H), 6.17 (brs, 1H), 3.99-3.90 (m, 2H), 3.35-3.23 (m, 2H), 3.00 (d, J=7.3 Hz, 2H), 2.94-2.87 (m, 1H), 2.04-1.88 (m, 1H), 1.53-1.46 (m, 4H), 1.48 (s, 9H), 0.92-0.84 (m, 2H), 0.63-0.55 (m, 2H). ESIMS m/z: 356 [M+H]$^+$.
Step 2
The above-obtained compound, i.e., 2-tert-butyl-N-cyclopropyl-3-(tetrahydropyran-4-ylmethyl)-imidazo[1,2-a]pyridine-7-carboxamide (30.0 mg, 0.0843 mmol) was dissolved in DMF (0.5 mL) under argon atmosphere. To this was added 60% sodium hydride (4.1 mg, 0.10 mmol) under ice-cooling, and then the mixture was stirred at room temperature for 1 hour. After addition of methyl iodide (53.0 μL, 0.851 mmol), the mixture was stirred at room temperature for another 1 hour. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=97/3), and the resulting crude crystals were reslurried with heptane to give the title compound 19 (25.9 mg, 0.0701 mmol, yield 83%).
$^1$H-NMR (δ ppm, CDCl$_3$): 7.88 (d, J=7.3 Hz, 1H), 7.73 (s, 1H), 6.99-6.94 (m, 1H), 4.00-3.91 (m, 2H), 3.37-3.24 (m, 2H), 3.11 (s, 3H), 3.00 (d, J=7.3 Hz, 2H), 2.95-2.85 (m, 1H), 2.03-1.87 (m, 1H), 1.57-1.42 (m, 4H), 1.49 (s, 9H), 0.76-0.67 (m, 2H), 0.60-0.52 (m, 2H). ESIMS m/z: 370 [M+H]$^+$.

EXAMPLE 20

2-tert-Butyl-N-ethyl-N-(2-methoxyethyl)-3-(tetrahydropyran-4-ylmethyl)imidazo[1,2-a]pyridine-7-carboxamide (Compound 20)

Except that 2-tert-butyl-3-(tetrahydropyran-4-ylmethyl) imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that N-(2-methoxyethyl)ethylamine was used instead of diethylamine, the same procedure as described in Example 1 was performed to give the title compound 20 (92.0 mg, 0.229 mmol, yield 72%).
$^1$H-NMR (δ ppm, CDCl$_3$): 7.89 (d, J=7.1 Hz, 1H), 7.56 (s, 1H), 6.84 (d, J=7.1 Hz, 1H), 4.02-3.91 (m, 2H), 3.69-3.49 (m, 6H), 3.39-3.24 (m, 2H), 3.35 (s, 3H), 2.99 (d, J=7.3 Hz, 2H), 2.08-1.89 (m, 1H), 1.58-1.45 (m, 4H), 1.49 (s, 9H), 1.19 (t, J=7.0 Hz, 3H). ESIMS m/z: 402 [M+H]$^+$.

EXAMPLE 21

2-tert-Butyl-N-(2-cyanoethyl)-N-methyl-3-(tetrahydropyran-4-ylmethyl)imidazo[1,2-a]pyridine-7-carboxamide (Compound 21)

Except that 2-tert-butyl-3-(tetrahydropyran-4-ylmethyl)imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that 3-methylamino-propiononitrile was used instead of diethylamine, the same procedure as described in Example 1 was performed to give the title compound 21 (90.0 mg, 0.235 mmol, yield 74%).

$^1$H-NMR (δ ppm, CDCl$_3$): 7.93 (d, J=6.9 Hz, 1H), 7.63 (s, 1H), 6.90 (dd, J=6.9, 1.7 Hz, 1H), 4.01-3.92 (m, 2H), 3.78 (t, J=6.5 Hz, 2H), 3.39-3.23 (m, 2H), 3.23 (s, 3H), 3.01 (d, J=7.4 Hz, 2H), 2.76 (t, J=6.5 Hz, 2H), 2.03-1.87 (m, 1H), 1.59-1.46 (m, 4H), 1.49 (s, 9H). ESIMS m/z: 383 [M+H]$^+$.

EXAMPLE 22

1-{2-tert-Butyl-3-(tetrahydropyran-4-ylmethyl)imidazo-[1,2-a]pyridine-7-carbonyl}-2-methylpiperidine (Compound 22)

Except that 2-tert-butyl-3-(tetrahydropyran-4-ylmethyl)imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that 2-methylpiperidine was used instead of diethylamine, the same procedure as described in Example 1 was performed to give the title compound 22 (190 mg, 0.438 mmol, yield 92%).

$^1$H-NMR (δ ppm, CDCl$_3$): 7.89 (dd, J=7.2, 0.7 Hz, 1H), 7.53 (dd, J=1.5, 0.7 Hz, 1H), 6.83 (dd, J=7.2, 1.5 Hz, 1H), 4.63 (brs, 1H), 4.18-4.06 (m, 1H), 4.00-3.91 (m, 2H), 3.36-3.25 (m, 2H), 3.11-3.01 (m, 1H), 2.99 (d, J=7.2 Hz, 2H), 2.01-1.87 (m, 1H), 1.75-1.63 (m, 4H), 1.56-1.48 (m, 6H), 1.48 (s, 9H), 1.26 (d, J=6.9 Hz, 3H). ESIMS m/z: 398 [M+H]$^+$.

EXAMPLE 23

1-{2-tert-Butyl-3-(tetrahydropyran-4-ylmethyl)imidazo-[1,2-a]pyridine-7-carbonyl}-2,5-dimethyl-3-pyrroline (Compound 23)

Except that 2-tert-butyl-3-(tetrahydropyran-4-ylmethyl)imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that 2,5-dimethyl-3-pyrroline was used instead of diethylamine, the same procedure as described in Example 1 was performed to give the title compound 23 (a diastereomer mixture, racemate) (59.2 mg, 0.150 mmol, yield 47%).

Diastereomer-a). $^1$H-NMR (δ ppm, CDCl$_3$): 7.91 (d, J=7.1 Hz, 1H), 7.78-7.75 (m, 1H), 7.01 (dd, J=7.1, 1.7 Hz, 1H), 5.75 (brs, 2H), 5.01 (brs, 2H), 4.00-3.91 (m, 2H), 3.36-3.25 (m, 2H), 3.00 (d, J=7.3 Hz, 2H), 2.01-1.88 (m, 1H), 1.55-1.46 (m, 4H), 1.49 (s, 9H), 1.32-1.22 (m, 3H), 0.99 (brs, 3H). Diastereomer-b). $^1$H-NMR (δ ppm, CDCl$_3$): 7.91 (d, J=7.1 Hz, 1H), 7.60-7.57 (m, 1H), 6.85 (dd, J=7.1, 1.7 Hz, 1H), 5.61 (brs, 2H), 4.83 (brs, 2H), 4.00-3.91 (m, 2H), 3.36-3.25 (m, 2H), 3.00 (d, J=7.3 Hz, 2H), 2.01-1.88 (m, 1H), 1.55-1.46 (m, 4H), 1.49 (s, 9H), 1.32-1.22 (m, 3H), 0.99 (brs, 3H).
ESIMS m/z: 396 [M+H]$^+$.

EXAMPLE 24

4-(2-tert-Butyl-3-(tetrahydropyran-4-ylmethyl)imidazo-[1,2-a]pyridine-7-carbonyl)thiomorpholine (Compound 24)

Except that 2-tert-butyl-3-(tetrahydropyran-4-ylmethyl)imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that thiomorpholine was used instead of diethylamine, the same procedure as described in Example 1 was performed to give the title compound 24 (98.0 mg, 0.244 mmol, yield 78%).

$^1$H-NMR (δ ppm, CDCl$_3$): 7.92 (d, J=7.1 Hz, 1H), 7.55 (s, 1H), 6.84 (d, J=7.1 Hz, 1H), 4.00-3.89 (m, 6H), 3.36-3.25 (m, 2H), 3.00 (d, J=7.3 Hz, 2H), 2.70-2.64 (m, 4H), 2.03-1.88 (m, 1H), 1.56-1.48 (m, 4H), 1.48 (s, 9H). ESIMS m/z: 402 [M+H]$^+$.

EXAMPLE 25

4-{2-tert-Butyl-3-(tetrahydropyran-4-ylmethyl)imidazo-[1,2-a]pyridine-7-carbonyl}-1,1-dioxothiomorpholine (Compound 25)

Except that 2-tert-butyl-3-(tetrahydropyran-4-ylmethyl)imidazo[1,2-a]-pyridine-7-carboxylic acid obtained in Reference Example 7 was used instead of 2-tert-butyl-3-cyclohexylmethylimidazo[1,2-a]pyridine-7-carboxylic acid and that 1,1-dioxo-thiomorpholine was used instead of diethylamine, the same procedure as described in Example 1 was performed to give the title compound 25 (82.0 mg, 0.189 mmol, yield 60%).

$^1$H-NMR (δ ppm, CDCl$_3$): 7.96 (d, J=7.1 Hz, 1H), 7.64-7.62 (m, 1H), 6.89 (dd, J=7.1, 1.7 Hz, 1H), 4.19-4.12 (m, 4H), 4.00-3.92 (m, 2H), 3.37-3.26 (m, 2H), 3.13-3.06 (m, 4H), 3.01 (d, J=7.3 Hz, 2H), 1.99-1.84 (m, 1H), 1.57-1.49 (m, 4H), 1.48 (s, 9H). ESIMS m/z: 434 [M+H]$^+$.

EXAMPLE 26

2-tert-Butyl-N,N-diethyl-3-(morpholin-4-ylmethyl)imidazo-[1,2-a]pyridine-7-carboxamide (Compound 26)

2-tert-Butyl-N,N-diethyl-3-hydroxymethylimidazo[1,2-a]-pyridine-7-carboxamide (31.3 mg, 0.103 mmol) obtained in Reference Example 22 was dissolved in thionyl chloride (1.0 mL), and then the mixture was heated under ref lux with stirring for 1 hour. After thionyl chloride was evaporated off in vacuo, the resulting residue was dissolved in acetonitrile (1.0 mL). To this was added morpholine (27.0 µL, 0.309 mmol), and then the mixture was heated under ref lux with stirring for 1 hour. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=95/5) to give the title compound 26 (29.4 mg, 0.079 mmol, yield 77%).

$^1$H-NMR (δ ppm, CDCl$_3$): 8.40 (d, J=7.1 Hz, 1H), 7.55-7.53 (m, 1H), 6.82 (dd, J=7.1, 1.5 Hz, 1H), 3.98 (s, 2H), 3.68-3.63 (m, 4H), 3.48 (q, J=7.3 Hz, 4H), 2.50-2.45 (m, 4H), 1.48 (s, 9H), 1.21 (t, J=7.3 Hz, 6H). ESIMS m/z: 373 [M+H]$^+$.

EXAMPLE 27

2-tert-Butyl-N,N-diethyl-3-(tetrahydropyran-2-ylmethyl)-imidazo[1,2-a]pyridine-7-carboxamide (Compound 27)

Except that the crude-purified 2-bromo-4,4-dimethyl-1-(tetrahydropyran-2-yl)pentan-3-one obtained in Reference Example 24 was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the title compound 27 (45.3 mg, 0.122 mmol, yield 45%).

$^1$H-NMR (δ ppm, CDCl$_3$): 8.20 (d, J=7.1 Hz, 1H), 7.51 (s, 1H), 6.76 (dd, J=7.1, 1.6 Hz, 1H), 3.95-3.86 (m, 1H), 3.59-3.41 (m, 1H), 3.47 (q, J=7.1 Hz, 4H), 3.35-3.04 (m, 3H), 1.52-1.46 (m, 6H), 1.47 (s, 9H), 1.20 (t, J=7.1 Hz, 6H). ESIMS m/z: 372 [M+H]$^+$.

EXAMPLE 28

2-tert-Butyl-N,N-diethyl-3-(thiophen-3-ylmethyl)imidazo-[1,2-a]pyridine-7-carboxamide (Compound 28)

Except that a mixture of 2-tert-butyl-3-(2,5-dibromothiophen-3-ylmethyl)-N,N-1-diethyl-imidazo[1,2-a]pyridine-7-carboxamide and 2-tert-butyl-3-(2,4-dibromothiophen-3-ylmethyl)-N,N-diethyl-imidazo[1,2-a]pyridine-7-carboxamide, which was obtained in Reference Example 28, was used instead of 4-(tetrahydropyran-4-yl)-2-butenoic acid ethyl ester, the same procedure as described in Reference Example 17 was performed to give the title compound 28 (17.3 mg, 0.047 mmol, yield 27%).

$^1$H-NMR (δ ppm, CDCl$_3$): 7.67 (d, J=6.9 Hz, 1H), 7.59-7.57 (m, 1H), 7.27 (dd, J=5.0, 3.0 Hz, 1H), 6.85 (d, J=5.0 Hz, 1H), 6.75-6.70 (m, 2H), 4.42 (s, 2H), 3.46 (q, J=7.2 Hz, 4H), 1.49 (s, 9H), 1.19 (t, J=7.2 Hz, 6H). ESIMS m/z: 370 [M+H]$^+$.

EXAMPLE 29

2-tert-Butyl-7-methylamino-3-(tetrahydropyran-4-ylmethyl)-imidazo[1,2-a]pyridine (Compound 29)

Except that 2-bromo-4,4-dimethyl-1-(tetrahydropyran-4-yl)pentan-3-one was used instead of 2-bromo-1-cyclohexyl-4,4-dimethylpentan-3-one and that 2-amino-4-methylaminopyridine obtained by a method described in a WO 2006/040520 pamphlet was used instead of 2-amino-4-cyanopyridine, the same procedure as described in Reference Example 2 was performed to give the title compound 29 (540 mg, 1.79 mmol, yield 50%).

$^1$H-NMR (δ ppm, CDCl$_3$): 7.56 (d, J=7.3 Hz, 1H), 6.52 (d, J=2.1 Hz, 1H), 6.19 (dd, J=7.3, 2.1 Hz, 1H), 4.00-3.91 (m, 2H), 3.84 (brs, 1H), 3.35-3.24 (m, 2H), 2.88 (d, J=7.4 Hz, 2H), 2.85 (s, 3H), 1.90-1.77 (m, 1H), 1.63-1.45 (m, 4H), 1.45 (s, 9H). ESIMS m/z: 302 [M+H]$^+$.

EXAMPLE 30

N-{2-tert-Butyl-3-(tetrahydropyran-4-ylmethyl)imidazo-[1,2-a]pyridin-7-yl}-3,N-dimethylbutanamide (Compound 30)

2-tert-Butyl-7-methylamino-3-(tetrahydropyran-4-ylmethyl)imidazo[1,2-a]pyridine (67.3 mg, 0.207 mmol) obtained in Example 29 was dissolved in dichloromethane (2.0 mL). To this were added triethylamine (160 μL, 1.15 mmol) and isovaleryl chloride (82.0 μL, 0.673 mmol) under argon atmosphere, and then the mixture was stirred at room temperature for 1 hour. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=95/5), and the resulting crude crystals were reslurried with heptane to give the title compound 30 (50.1 mg, 0.130 mmol, yield 58%).

$^1$H-NMR (δ ppm, CDCl$_3$): 7.88 (d, J=7.3 Hz, 1H), 7.39 (d, J=1.8 Hz, 1H), 6.61 (dd, J=7.3, 1.8 Hz, 1H), 4.02-3.93 (m, 2H), 3.38-3.28 (m, 2H), 3.28 (s, 3H), 3.00 (d, J=7.3 Hz, 2H), 2.17-2.10 (m, 3H), 2.02-1.85 (m, 1H), 1.58-1.51 (m, 4H), 1.49 (s, 9H), 0.88 (d, J=6.1 Hz, 6H). ESIMS m/z: 386 [M+H]$^+$.

EXAMPLE 31

1-[2-tert-Butyl-3-(tetrahydropyran-4-ylmethyl)imidazo-[1,2-a]pyridin-7-yl]-3-isopropyl-1-methylurea (Compound 31)

2-tert-Butyl-7-methylamino-3-(tetrahydropyran-4-ylmethyl)imidazo[1,2-a]pyridine (100 mg, 0.332 mmol) obtained in Example 29 was dissolved in DMF (1.0 mL). To this was added isopropyl isocyanate (40.0 μL, 0.407 mmol) under argon atmosphere, and then the mixture was stirred at 50° C. overnight. After addition of aqueous sodium bicarbonate solution, the mixture was extracted with ethyl acetate. The organic phase was washed with saturated brine and dried over anhydrous sodium sulfate, and then the solvent was evaporated of f in vacuo. The residue was purified by column chromatography on silica gel (chloroform/methanol=95/5), and the resulting crude crystals were reslurried with heptane to give the title compound 31 (51.4 mg, 0.133 mmol, yield 40%).

$^1$H-NMR (δ ppm, CDCl$_3$): 7.86 (d, J=7.3 Hz, 1H), 7.39 (d, J=2.0 Hz, 1H), 6.70 (dd, J=7.3, 2.1 Hz, 1H), 4.34 (d, J=7.3 Hz, 1H), 4.06-3.91 (m, 3H), 3.39-3.27 (m, 2H), 3.27 (s, 3H), 2.99 (d, J=7.3 Hz, 2H), 2.02-1.83 (m, 1H), 1.61-1.52 (m, 4H), 1.48 (s, 9H), 1.09 (d, J=6.6 Hz, 6H). ESIMS m/z: 387 [M+H]$^+$.

EXAMPLE 32

N-[2-tert-Butyl-3-(tetrahydropyran-4-ylmethyl)imidazo-[1,2-a]pyridin-7-yl]-N-methyl-methanesulfonamide (Compound 32)

2-tert-Butyl-7-methylamino-3-(tetrahydropyran-4-ylmethyl)imidazo[1,2-a]pyridine (50.0 mg, 0.166 mmol) obtained in Example 29 was dissolved in 1,2-dichloroethane (1.0 mL). To this were added methanesulfonyl chloride (64.0 μL, 0.827 mmol) and N,N-dimethyl-4-aminopyridine (6.0 mg, 0.050 mmol) under argon atmosphere, and then the mixture was stirred at 50° C. overnight. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=95/5) to give the title compound 32 (6.3 mg, 0.017 mmol, yield 10%).

$^1$H-NMR (δ ppm, CDCl$_3$): 7.82 (d, J=7.4 Hz, 1H), 7.45 (d, J=2.1 Hz, 1H), 7.02 (dd, J=7.4, 2.1 Hz, 1H), 4.02-3.93 (m, 2H), 3.38-3.26 (m, 2H), 3.35 (s, 3H), 2.98 (d, J=7.3 Hz, 2H), 2.87 (s, 3H), 2.00-1.83 (m, 1H), 1.58-1.48 (m, 4H), 1.47 (s, 9H). ESIMS m/z: 380 [M+H]$^+$.

EXAMPLE 33

N-[2-tert-Butyl-3-(tetrahydropyran-4-ylmethyl)imidazo-[1,2-a]pyridin-7-yl]-N,N',N'-trimethylsulfamide (Compound 33)

2-tert-Butyl-7-methylamino-3-(tetrahydropyran-4-ylmethyl)imidazo[1,2-a]pyridine (50.0 mg, 0.166 mmol)

obtained in Example 29 was dissolved in acetonitrile (1.0 mL). To this were added dimethyl sulfamoyl chloride (36.0 µL, 0.335 mmol), triethylamine (70 µL, 0.501 mmol) and N,N-dimethyl-4-aminopyridine (6.0 mg, 0.050 mmol) under argon atmosphere, and then the mixture was stirred at 50° C. overnight. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=95/5) to give the title compound 33 (3.9 mg, 0.0095 mmol, yield 6%).

$^1$H-NMR (δ ppm, CDCl$_3$): 7.79 (d, J=7.6 Hz, 1H), 7.44 (d, J=2.3 Hz, 1H), 7.01 (dd, J=7.6, 2.3 Hz, 1H), 4.00-3.91 (m, 2H), 3.39-3.25 (m, 2H), 3.29 (s, 3H), 2.96 (d, J=7.4 Hz, 2H), 2.85 (s, 6H), 1.99-1.85 (m, 1H), 1.56-1.48 (m, 4H), 1.47 (s, 9H). ESIMS m/z: 409 [M+H]$^+$.

REFERENCE EXAMPLE 1

2-Bromo-1-cyclohexyl-4,4-dimethylpentan-3-one

1-Cyclohexyl-4,4-dimethylpentan-3-one (3.24 g, 16.5 mmol) obtained by a method described in JP-A No. 62-039581 was dissolved in ethanol (40 mL). To this was added tetrabutylammonium tribromide (8.78 g, 18.2 mmol), and then the mixture was stirred under ref lux for 1 hour. Then, the mixture was allowed to stand and cool to room temperature. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by column chromatography on silica gel (hexane/ethyl acetate=99/1) to give the title compound (3.65 g, 13.3 mmol, yield 80%).

$^1$H-NMR (δ ppm, CDCl$_3$): 4.75 (dd, J=9.3, 5.2 Hz, 1H), 1.85-1.39 (m, 7H), 1.33-1.16 (m, 4H), 1.22 (s, 9H), 1.02-0.81 (m, 2H).

REFERENCE EXAMPLE 2

2-tert-Butyl-3-cyclohexylmethylimidazo[1,2-a]pyridine-7-carbonitrile

2-Bromo-1-cyclohexyl-4,4-dimethylpentan-3-one (2.50 g, 9.08 mmol) obtained in Reference Example 1 was dissolved in n-butanol (15 mL). To this was added 2-amino-4-cyanopyridine (1.30 g, 10.9 mmol), and then the mixture was stirred under reflux overnight. Then, the mixture was allowed to stand and cool to room temperature. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by column chromatography on silica gel (hexane/ethyl acetate=90/10) to give the title compound (1.31 g, 4.43 mmol, yield 49%).

$^1$H-NMR (δ ppm, CDCl$_3$): 7.97-9.92 (m, 2H), 6.92-6.85 (m, 1H), 2.93 (d, J=7.1 Hz, 2H), 1.75-1.50 (m, 6H), 1.48 (s, 9H), 1.31-1.03 (m, 5H). ESIMS m/z: 296 [M+H]$^+$.

REFERENCE EXAMPLE 3

2-tert-Butyl-3-cyclohexylmethylimidazo[1,2-a]pyridine-7-carboxylic acid 2-tert-Butyl-3-cyclohexylmethylimidazo[1,2-a]pyridine-7-carbonitrile (1.20 g, 4.05 mmol) obtained in Reference Example 2, and sodium hydroxide (471 mg, 11.8 mmol) were dissolved in a 70% aqueous solution of ethanol (4.5 mL), and then the mixture was heated under reflux for 3 hours. After the mixture was cooled down to 0° C., 3 mol/L hydrochloric acid (4 mL) was slowly added thereto. The precipitate was separated by filtration to give the title compound (0.854 g, 2.70 mmol, yield 67%).

$^1$H-NMR (δ ppm, CDCl$_3$): 8.32 (d, J=7.3 Hz, 1H), 7.98-7.95 (m, 1H), 7.24 (dd, J=7.3, 1.4 Hz, 1H), 2.95 (d, J=7.1 Hz, 2H), 1.71-1.44 (m, 6H), 1.39 (s, 9H), 1.19-1.02 (m, 5H). ESIMS m/z: 315 [M+H]$^+$.

REFERENCE EXAMPLE 4

4,4-Dimethyl-1-(tetrahydropyran-4-yl)pentan-3-one 3-(Tetrahydropyran-4-yl)propionic acid (4.00 g, 25.3 mmol) obtained by a method described in JP-A No. 2001-019672 was dissolved in thionyl chloride (40 mL), and then the mixture was stirred under reflux for 1 hour. The solvent was evaporated off in vacuo and the resulting residue was dissolved in THF (80 mL) under argon atmosphere. After addition of cuprous chloride (125 mg, 1.26 mmol), the mixture was cooled down to 0° C. To this was added dropwise a solution of tert-butyl magnesium chloride in THF (16.4 mL, 27.9 mmol) so slowly that an internal temperature might not exceed 10° C. After the end of the dropwise addition, the mixture was stirred at room temperature for 2 hours. Then, the mixture was cooled down to 0° C. After addition of aqueous ammonium chloride solution, the mixture was extracted with ethyl acetate. The organic phase was washed with saturated brine and dried over anhydrous magnesium sulfate, and then the solvent was evaporated off in vacuo. The residue was purified by column chromatography on silica gel (hexane/ethyl acetate=80/20) to give the title compound (4.36 g, 22.0 mmol, yield 87%).

$^1$H-NMR (δ ppm, CDCl$_3$): 3.98-3.92 (m, 2H), 3.42-3.30 (m, 2H), 2.50 (t, J=7.3 Hz, 2H), 1.61-1.45 (m, 5H), 1.34-1.26 (m, 2H), 1.14 (s, 9H).

REFERENCE EXAMPLE 5

2-Bromo-4,4-dimethyl-1-(tetrahydropyran-4-yl)pentan-3-one

Except that 4,4-dimethyl-1-(tetrahydropyran-4-yl)pentan-3-one obtained in Reference Example 4 was used instead of 1-cyclohexyl-4,4-dimethylpentan-3-one, the same procedure as described in Reference Example 1 was performed to give the title compound (5.56 g, 20.1 mmol, yield 91%).

$^1$H-NMR (δ ppm, CDCl$_3$): 4.73 (dd, J=9.1, 5.3 Hz, 1H), 4.00-3.93 (m, 2H), 3.45-3.32 (m, 2H), 2.05-1.95 (m, 1H), 1.76-1.14 (m, 6H), 1.25 (s, 9H).

REFERENCE EXAMPLE 6

2-tert-Butyl-3-(tetrahydropyran-4-ylmethyl)imidazo[1,2-a]-pyridine-7-carbonitrile Except that 2-bromo-4,4-dimethyl-1-(tetrahydropyran-4-yl)pentan-3-one obtained in Reference Example 5 was used instead of 2-bromo-1-cyclohexyl-4,4-dimethylpentan-3-one, the same procedure as described in Reference Example 2 was performed to give the title compound (501 mg, 1.68 mmol, yield 47%).

¹H-NMR (δ ppm, CDCl₃): 7.96-7.94 (m, 2H), 6.93-6.90 (m, 1H), 4.01-3.92 (m, 2H), 3.36-3.25 (m, 2H), 3.02 (d, J=7.3 Hz, 2H), 2.03-1.87 (m, 1H), 1.56-1.47 (m, 4H), 1.49 (s, 9H). ESIMS m/z: 298 [M+H]⁺.

REFERENCE EXAMPLE 7

2-tert-Butyl-3-(tetrahydropyran-4-ylmethyl)imidazo[1,2-a]-pyridine-7-carboxylic acid Except that 2-tert-butyl-3-(tetrahydropyran-4-ylmethyl)imidazo[1,2-a]-pyridine-7-carbonitrile obtained in Reference Example 6 was used instead of 2-tert-butyl-3-cyclohexylmethylimidazo[1,2-a]pyridine-7-carbonitrile, the same procedure as described in Reference Example 3 was performed to give the title compound (11.0 g, 34.8 mmol, yield 71%).
¹H-NMR (δ ppm, CDCl₃): 8.52 (s, 1H), 7.87 (d, J=7.1 Hz, 1H), 7.48 (d, J=7.1 Hz, 1H), 3.96-3.89 (m, 2H), 3.35-3.21 (m, 2H), 3.00 (d, J=7.1 Hz, 2H), 2.00-1.86 (m, 1H), 1.52-1.46 (m, 4H), 1.50 (s, 9H). ESIMS m/z: 317 [M+H]⁺.

REFERENCE EXAMPLE 8

2-Amino-N,N-diethyl-pyridine-4-carboxamide

Except that 2-aminopyridine-4-carboxylic acid was used instead of 2-tert-butyl-3-cyclohexylmethylimidazo[1,2-a]pyridine-7-carboxylic acid, the same procedure as described in Example 1 was performed to give the title compound (750 mg, 3.88 mmol, yield 53%).
¹H-NMR (δ ppm, CDCl₃): 8.11 (d, J=5.1 Hz, 1H), 6.59 (dd, J=5.1, 1.3 Hz, 1H), 6.46-6.44 (m, 1H), 4.52 (br, 2H), 3.52 (q, J=7.1 Hz, 2H), 3.23 (q, J=7.1 Hz, 2H), 1.23 (t, J=7.1 Hz, 3H), 1.11 (t, J=7.1 Hz, 3H).

REFERENCE EXAMPLE 9

6-Aminopyrimidine-4-carboxylic acid propyl ester

A mixture of 6-chloro-4-aminopyrimidine (2.00 g, 15.4 mmol), palladium acetate (361 mg, 1.61 mmol), 1,3-bis(diphenylphosphino)propane (631 mg, 1.52 mmol), and potassium carbonate (2.55 g, 18.5 mmol) in n-propanol (45 mL) and DMF (15 mL) was stirred at 90° C. under carbon monoxide atmosphere. The mixture was allowed to stand and cool to room temperature, and then filtered through Celite. Aqueous sodium bicarbonate solution was added to the filtrate, which was extracted with ethyl acetate. The organic phase was washed with saturated brine and dried over anhydrous magnesium sulfate, and then the solvent was evaporated off in vacuo. The residue was purified by column chromatography on silica gel (chloroform/methanol=100/1 to 50/1) to give the title compound (1.86 g, 10.3 mmol, yield 67%).
¹H-NMR (δ ppm, CDCl₃): 8.71 (d, J=1.2 Hz, 1H), 7.17 (d, J=1.2 Hz, 1H), 5.16 (br, 2H), 4.35 (t, J=6.9 Hz, 2H), 1.83 (tq, J=7.4, 6.9 Hz, 2H), 1.02 (t, J=7.4 Hz, 3H).

REFERENCE EXAMPLE 10

2-tert-Butyl-3-cyclohexylmethylimidazo[1,2-c]pyrimidine-7-carboxylic acid propyl ester The mixture of 2-bromo-1-cyclohexyl-4,4-dimethylpentan-3-one (828 mg, 3.01 mmol) obtained in Reference Example 1, and 6-aminopyrimidine-4-carboxylic acid propyl ester (824 mg, 4.52 mmol) obtained in Reference Example 9 was stirred at 130° C. overnight. Then, the mixture was allowed to stand and cool to room temperature. After addition of aqueous sodium bicarbonate solution, the mixture was extracted with ethyl acetate. The organic phase was washed with saturated brine and dried over anhydrous magnesium sulfate, and then the solvent was evaporated off in vacuo. The residue was purified by column chromatography on silica gel (chloroform/methanol=90/10 to 70/30) to give the title compound (231 mg, 0.650 mmol, yield 21%).
¹H-NMR (δ ppm, CDCl₃): 8.87 (d, J=1.3 Hz, 1H), 8.33 (d, J=1.3 Hz, 1H), 4.36 (t, J=6.8 Hz, 2H), 3.00 (d, J=7.1 Hz, 2H), 1.84 (tq, J=7.4, 6.8 Hz, 2H), 1.77-1.58 (m, 6H), 1.48 (s, 9H), 1.28-1.04 (m, 5H), 1.04 (t, J=7.4 Hz, 3H). ESIMS m/z: 358 [M+H]⁺.

REFERENCE EXAMPLE 11

2-tert-Butyl-3-cyclohexylmethylimidazo[1,2-c]pyrimidine-7-carboxylic acid 2-tert-Butyl-3-cyclohexylmethylimidazo[1,2-c]-pyrimidine-7-carboxylic acid propyl ester (177 mg, 0.496 mmol) obtained in Reference Example 10, and lithium hydroxide monohydrate (23.0 mg, 0.550 mmol) were dissolved in a 50% aqueous solution of ethanol (3 mL). Then, this mixture was stirred at room temperature for 1 hour. After the mixture was cooled down to 0° C., 1 mol/L hydrochloric acid (0.5 mL) was slowly added thereto. The precipitate was separated by filtration to give the title compound (131 mg, 0.420 mmol, yield 84%).
¹H-NMR (δ ppm, DMSO-d₆): 9.26 (s, 1H), 8.04 (s, 1H), 3.04 (d, J=7.0 Hz, 2H), 1.70-1.48 (m, 6H), 1.40 (s, 9H), 1.17-1.08 (m, 5H). ESIMS m/z: 316 [M+H]⁺.

REFERENCE EXAMPLE 12

2-tert-Butyl-3-(tetrahydropyran-4-ylmethyl)imidazo[1,2-c]-pyrimidine-7-carboxylic acid propyl ester Except that 2-bromo-4,4-dimethyl-1-(tetrahydropyran-4-yl)pentan-3-one obtained in Reference Example 5 was used instead of 2-bromo-1-cyclohexyl-4,4-dimethylpentan-3-one and that 6-aminopyrimidine-4-carboxylic acid propyl ester obtained in Reference Example 9 was used instead of 2-amino-4-cyanopyridine, the same procedure as described in Reference Example 2 was performed to give the title compound (286 mg, 0.800 mmol, yield 22%).
¹H-NMR (δ ppm, CDCl₃): 8.89 (d, J=1.1 Hz, 1H), 8.34 (d, J=1.1 Hz, 1H), 4.37 (t, J=6.8 Hz, 2H), 4.01-3.94 (m, 2H), 3.35-3.25 (m, 2H), 3.09 (d, J=7.3 Hz, 2H), 2.02-1.80 (m, 3H), 1.58-1.47 (m, 4H), 1.49 (s, 9H), 1.04 (t, J=7.4 Hz, 3H). ESIMS m/z: 360 [M+H]⁺.

REFERENCE EXAMPLE 13

2-tert-Butyl-3-(tetrahydropyran-4-ylmethyl)imidazo[1,2-c]-pyrimidine-7-carboxylic acid Except that 2-tert-butyl-3-(tetrahydropyran-4-ylmethyl)imidazo[1,2-c]-pyrimidine-7-carboxylic acid propyl ester obtained in Reference Example 12 was used instead of 2-tert-butyl-3-cyclohexylmethylimidazo[1,2-a]pyridine-7-carbonitrile, the same procedure as described in Reference Example 3 was performed to give the title compound (793 mg, 0.250 mmol, yield 61%).

¹H-NMR (δ ppm, CDCl₃): 8.92 (d, J=1.0 Hz, 1H), 8.44 (d, J=1.0 Hz, 1H), 4.03-3.95 (m, 2H), 3.40-3.28 (m, 2H), 3.12 (d, J=7.4 Hz, 2H), 2.04-1.90 (m, 1H), 1.56-1.47 (m, 4H), 1.51 (s, 9H). ESIMS m/z: 318 [M+H]⁺.

REFERENCE EXAMPLE 14

6-Cyclohexyl-2,2-dimethylhexan-3-one

Except that 4-cyclohexyl butyric acid was used instead of 3-(tetrahydropyran-4-yl)propionic acid, the same procedure as described in Reference Example 4 was performed to give the title compound (1.07 g, 5.09 mol, yield 87%).
¹H-NMR (δ ppm, CDCl₃): 2.44 (t, J=7.3 Hz, 2H), 1.81-0.76 (m, 15H), 1.13 (s, 9H).

REFERENCE EXAMPLE 15

4-Bromo-6-cyclohexyl-2,2-dimethylhexan-3-one

Except that 6-cyclohexyl-2,2-dimethylhexan-3-one obtained in Reference Example 14 was used instead of 1-cyclohexyl-4,4-dimethylpentan-3-one, the same procedure as described in Reference Example 1 was performed to give the title compound (1.31 g, 4.53 mmol, yield 90%).
¹H-NMR (δ ppm, CDCl₃): 4.57 (t, J=7.3 Hz, 1H), 2.03-0.90 (m, 15H), 1.23 (s, 9H).

REFERENCE EXAMPLE 16

4-(Tetrahydropyran-4-yl)-2-butenoic acid ethyl ester

60% sodium hydride (172 mg, 4.30 mmol) was suspended in THF (10 mL) under argon atmosphere. To this was gently added triethyl phosphonoacetate (860 μL, 4.34 mmol) under ice-cooling, and then the mixture was stirred at room temperature for 10 minutes. A solution of (tetrahydropyran-4-yl)-acetaldehyde (500 mg, 3.90 mol) in THF (10 mL) was added to the mixture, which was stirred for 1 hour. After addition of aqueous ammonium chloride solution, the mixture was extracted with ethyl acetate. The organic phase was washed with saturated brine and dried over anhydrous sodium sulfate, and then the solvent was evaporated of f in vacuo. The residue was purified by column chromatography on silica gel (hexane/ethyl acetate=80/20) to give the title compound (523 mg, 2.64 mmol, yield 68%).
¹H-NMR (δ ppm, CDCl₃): 6.92 (dt, J=15.5, 7.6 Hz, 1H), 5.83 (dt, J=15.5, 1.4 Hz, 1H), 4.19 (q, J=7.1 Hz, 2H), 4.00-3.91 (m, 2H), 3.43-3.31 (m, 2H), 2.20-2.12 (m, 2H), 1.76-1.57 (m, 3H), 1.45-1.22 (m, 2H), 1.29 (t, J=7.1 Hz, 3H).

REFERENCE EXAMPLE 17

4-(Tetrahydropyran-4-yl)butyric acid ethyl ester 4-(Tetrahydropyran-4-yl)-2-butenoic acid ethyl ester (522 mg, 2.63 mmol) obtained in Reference Example 16 was dissolved in ethanol (5.0 mL) under argon atmosphere. To this was added 10% palladium-carbon (300 mg), and then the mixture was stirred under hydrogen atmosphere at room temperature for 1 hour. The mixture was filtered through Celite, and the solvent was evaporated off in vacuo. The residue was purified by column chromatography on silica gel (hexane/ethyl acetate=90/10) to give the title compound (431 mg, 2.15 mmol, yield 82%).

¹H-NMR (δ ppm, CDCl₃): 4.13 (q, J=7.1 Hz, 2H), 3.99-3.90 (m, 2H), 3.42-3.30 (m, 2H), 2.29 (t, J=7.4 Hz, 2H), 1.70-1.22 (m, 9H), 1.26 (t, J=7.1 Hz, 3H).

REFERENCE EXAMPLE 18

4-(Tetrahydropyran-4-yl)butyric acid

Except that 4-(tetrahydropyran-4-yl)butyric acid ethyl ester obtained in Reference Example 17 was used instead of 2-tert-butyl-3-cyclohexylmethylimidazo[1,2-c]pyrimidine-7-carboxylic acid propyl ester, the same procedure as described in Reference Example 11 was performed to give the title compound (369 mg, 2.14 mmol, yield 99%).
¹H-NMR (δ ppm, CDCl₃): 4.00-3.92 (m, 2H), 3.42-3.31 (m, 2H), 2.35 (t, J=7.4 Hz, 2H), 1.72-1.42 (m, 5H), 1.36-1.20 (m, 4H).

REFERENCE EXAMPLE 19

2,2-Dimethyl-6-(tetrahydropyran-4-yl)hexan-3-one

Except that 4-(tetrahydropyran-4-yl)butyric acid obtained in Reference Example 18 was used instead of 3-(tetrahydropyran-4-yl)propionic acid, the same procedure as described in Reference Example 4 was performed to give the title compound (415 mg, 1.95 mol, yield 91%).
¹H-NMR (δ ppm, CDCl₃): 3.98-3.90 (m, 2H), 3.42-3.31 (m, 2H), 2.47 (t, J=7.2 Hz, 2H), 1.63-1.37 (m, 5H), 1.35-1.15 (m, 4H), 1.13 (s, 9H).

REFERENCE EXAMPLE 20

4-Bromo-2,2-dimethyl-6-(tetrahydropyran-4-yl)hexan-3-one

Except that 2,2-dimethyl-6-(tetrahydropyran-4-yl)hexan-3-one obtained in Reference Example 19 was used instead of 1-cyclohexyl-4,4-dimethylpentan-3-one, the same procedure as described in Reference Example 1 was performed to give the title compound (506 mg, 1.73 mmol, yield 87%).
¹H-NMR (δ ppm, CDCl₃): 4.58 (t, J=7.2 Hz, 1H), 3.99-3.91 (m, 2H), 3.42-3.30 (m, 2H), 2.09-1.91 (m, 1H), 1.24-1.24 (m, 8H), 1.60 (s, 9H).

REFERENCE EXAMPLE 21

2-tert-Butyl-N,N-diethyl-imidazo[1,2-a]pyridine-7-carboxamide

Except that 1-bromopinacolone was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the title compound (114 mg, 0.415 mmol, yield 80%).
¹H-NMR (δ ppm, CDCl₃): 8.07 (dd, J=6.9, 1.0 Hz, 1H), 7.56-7.54 (m, 1H), 7.38 (s, 1H), 6.79 (dd, J=6.9, 1.6 Hz, 1H), 3.47 (q, J=7.1 Hz, 4H), 1.41 (s, 9H), 1.20 (t, J=7.1 Hz, 6H). ESIMS m/z: 274 [M+H]⁺.

REFERENCE EXAMPLE 22

2-tert-Butyl-N,N-diethyl-3-hydroxymethylimidazo[1,2-a]-pyridine-7-carboxamide 2-tert-Butyl-N,N-diethyl-imidazo[1,2-a]pyridine-7-carboxamide (2.00 g, 7.32 mmol) obtained in Reference Example 21 was added to a mixed solvent of acetic acid (5.0 mL) and formalin (20 mL), and the mixture was stirred at 50° C. overnight. After addition of aqueous sodium bicarbonate solution, the mixture was extracted with ethyl acetate. The organic phase was washed with saturated brine and dried over anhydrous sodium sulfate, and then the solvent was evaporated off in vacuo. The residue was purified by column chromatography on silica gel (chloroform/methanol=95/5) to give the title compound (1.85 g, 6.10 mmol, yield 83%).

$^1$H-NMR (δ ppm, CDCl$_3$): 8.15 (d, J=6.9 Hz, 1H), 7.54 (s, 1H), 6.76 (d, J=6.9 Hz, 1H), 5.10 (s, 2H), 3.45 (q, J=7.3 Hz, 4H), 1.48 (s, 9H), 1.20 (t, J=7.3 Hz, 6H). ESIMS m/z: 304 [M+H]$^+$.

REFERENCE EXAMPLE 23

4,4-Dimethyl-1-(tetrahydropyran-2-yl)pentan-3-one

Except that 3-(tetrahydropyran-2-yl)propionic acid was used instead of 3-(tetrahydropyran-4-yl)propionic acid, the same procedure as described in Reference Example 4 was performed to give the title compound (160 mg, 0.807 mmol, yield 15%).

$^1$H-NMR (δ ppm, CDCl$_3$): 3.99-3.89 (m, 1H), 3.43-3.28 (m, 1H), 3.24-3.12 (m, 1H), 2.64-2.56 (m, 2H), 1.78-1.25 (m, 8H), 1.13 (s, 9H).

REFERENCE EXAMPLE 24

2-Bromo-4,4-dimethyl-1-(tetrahydropyran-2-yl)pentan-3-one

Except that 4,4-dimethyl-1-(tetrahydropyran-2-yl)pentan-3-one obtained in Reference Example 23 was used instead of 1-cyclohexyl-4,4-dimethylpentan-3-one, the same procedure as described in Reference Example 1 was performed to give the title compound as a crude product (66.6 mg, 0.240 mmol, yield 85%).

REFERENCE EXAMPLE 25

4,4-Dimethyl-1-(thiophen-3-yl)-1-penten-3-one

3-Thiophene carbaldehyde (500 μL, 5.71 mmol) and 3,3-dimethylbutan-2-one (710 μL, 5.71 mmol) were dissolved in methanol (5.0 mL). To this was added sodium methoxide (340 mg, 6.29 mmol), and then the mixture was stirred under reflux overnight. After addition of water, the mixture was extracted with ethyl acetate. The organic phase was washed with saturated brine and dried over anhydrous sodium sulfate, and then the solvent was evaporated off in vacuo. The residue was purified by column chromatography on silica gel (hexane/ethyl acetate 95/5) to give the title compound (904 mg, 4.65 mmol, yield 81%).

$^1$H-NMR (δ ppm, CDCl$_3$): 7.67 (d, J=15.5 Hz, 1H), 7.55-7.52 (m, 1H), 7.35-7.33 (m, 2H), 6.94 (d, J=15.5 Hz, 1H), 1.22 (s, 9H).

REFERENCE EXAMPLE 26

4,4-Dimethyl-1-(thiophen-3-yl)pentan-3-one

Except that 4,4-dimethyl-1-(thiophen-3-yl)-1-penten-3-one obtained in Reference Example 25 was used instead of 4-(tetrahydropyran-4-yl)-2-butenoic acid ethyl ester, the same procedure as described in Reference Example 17 was performed to give the title compound (649 mg, 3.31 mmol, yield 72%).

$^1$H-NMR (δ ppm, CDCl$_3$): 7.24 (dd, J=4.9, 3.1 Hz, 1H), 6.96-6.91 (m, 2H), 2.94-2.87 (m, 2H), 2.83-2.76 (m, 2H), 1.12 (s, 9H).

REFERENCE EXAMPLE 27

A mixture of 2-bromo-1-(2,5-dibromothiophen-3-yl)-4,4-dimethylpentan-3-one and 2-bromo-1-(2,4-dibromothiophen-3-yl)-4,4-dimethylpentan-3-one Except that 4,4-dimethyl-1-(thiophen-3-yl)pentan-3-one obtained in Reference Example 26 was used instead of 1-cyclohexyl-4,4-dimethylpentan-3-one, the same procedure as described in Reference Example 1 was performed to give the two title compounds as a mixture (135 mg, 0.312 mmol, yield 11%).

a) $^1$H-NMR (δ ppm, CDCl$_3$): 6.78 (s, 1H), 4.80-4.73 (m, 1H), 3.38-3.02 (m, 2H), 1.10 (s, 9H).
b) $^1$H-NMR (δ ppm, CDCl$_3$): 6.76 (s, 1H), 4.80-4.73 (m, 1H), 3.38-3.02 (m, 2H), 1.10 (s, 9H).

REFERENCE EXAMPLE 28

A mixture of 2-tert-butyl-3-(2,5-dibromothiophen-3-ylmethyl)-N,N-1-diethyl-imidazo[1,2-a]pyridine-7-carboxamide and 2-tert-butyl-3-(2,4-dibromothiophen-3-ylmethyl)-N,N-1-diethyl-imidazo[1,2-a]pyridine-7-carboxamide Except that a mixture of 2-bromo-1-(2,5-dibromothiophen-3-yl)-4,4-dimethylpentan-3-one and 2-bromo-1-(2,4-dibromothiophen-3-yl)-4,4-dimethylpentan-3-one, which was obtained in Reference Example 27, was used instead of 2-bromo-1-cyclohexyl-4,4-dimethylpentan-3-one and that 2-amino-N,N-diethyl-pyridine-4-carboxamide obtained in Reference Example 8 was used instead of 2-amino-4-cyanopyridine, the same procedure as described in Reference Example 2 was performed to give the two title compounds as a mixture (89.4 mg, 0.170 mol, yield 52%).

Isomer-a) $^1$H-NMR (δ ppm, CDCl$_3$): 7.63-7.58 (m, 2H), 6.83-6.78 (m, 1H), 6.24 (s, 1H), 4.26 (s, 2H), 3.47 (q, J=6.9 Hz, 4H), 1.50 (s, 9H), 1.20 (t, J=7.1 Hz, 6H).
Isomer-b) $^1$H-NMR (δ ppm, CDCl$_3$): 7.63-7.58 (m, 2H), 6.83-6.78 (m, 1H), 6.24 (s, 1H), 4.26 (s, 2H), 3.47 (q, J=7.1 Hz, 4H), 1.50 (s, 9H), 1.20 (t, J=7.1 Hz, 6H).
ESIMS m/z: 526, 528, 530 [M+H]$^+$.

REFERENCE EXAMPLE 29

2-tert-Butyl-7-methylamino-3-(tetrahydropyran-4-ylmethyl)-imidazo[1,2-a]pyridine Except that 2-bromo-4,4-dimethyl-1-(tetrahydropyran-4-yl)pentan-3-one was used instead of 2-bromo-1-cyclohexyl-4,4-dimethylpentan-3-one and that 2-amino-4-methylaminopyridine obtained by a method described in a WO 2006/040520 pamphlet was used instead of 2-amino-4-cyanopyridine, the same procedure as described in Reference Example 2 was performed to give the title compound (540 mg, 1.79 mmol, yield 50%).

$^1$H-NMR (δ ppm, CDCl$_3$): 7.56 (d, J=7.3 Hz, 1H), 6.52 (d, J=2.1 Hz, 1H), 6.19 (dd, J=7.3, 2.1 Hz, 1H), 4.00-3.91 (m, 2H), 3.84 (brs, 1H), 3.35-3.24 (m, 2H), 2.88 (d, J=7.4 Hz, 2H), 2.85 (s, 3H), 1.90-1.77 (m, 1H), 1.63-1.45 (m, 4H), 1.45 (s, 9H). ESIMS m/z: 302 [M+H]$^+$.

Industrial Applicability

According to the present invention, a novel fused heterocycle derivative or a pharmaceutically acceptable salt thereof which has an effect to modulate a CB2 receptor and is useful as a therapeutic and/or preventive agent for a pain or the like, can be provided.

The invention claimed is:

1. A fused heterocycle compound represented by formula (I):

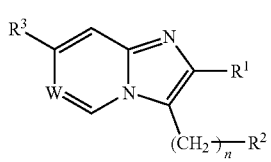

wherein $R^1$ represents optionally substituted lower alkyl, or optionally substituted cycloalkyl;
$R^2$ represents optionally substituted cycloalkyl, or an optionally substituted aliphatic heterocyclic group;
$R^3$ represents
(i) —C(=Z) $R^4$
(wherein $R^4$ represents optionally substituted lower alkyl, optionally substituted lower alkenyl, optionally substituted cycloalkyl, optionally substituted aralkyl, optionally substituted aryl, an optionally substituted heteroaromatic group, or an optionally substituted aliphatic heterocyclic group, and Z represents an oxygen atom or a sulfur atom), or
(ii) —C(=Z)NR$^5$R$^6$
(wherein $R^5$ and $R^6$ may be the same or different and each represents a hydrogen atom, optionally substituted lower alkyl, optionally substituted lower alkenyl, optionally substituted cycloalkyl, optionally substituted aralkyl, optionally substituted aryl, an optionally substituted heteroaromatic group, or an optionally substituted aliphatic heterocyclic group or $R^5$ and $R^6$ together with the adjacent nitrogen atom thereto form an optionally substituted nitrogen-containing heterocyclic group, and Z has the same definition as described above);
n represents an integer of 1 to 3; and
W represents a nitrogen atom or C—R$^{15}$
(wherein $R^{15}$ represents a hydrogen atom, halogen or lower, alkyl),
or a pharmaceutically acceptable salt thereof.

2. The fused heterocycle compound or the pharmaceutically acceptable salt thereof according to claim 1, wherein $R^1$ is optionally substituted tertiary lower alkyl, or optionally substituted tertiary cycloalkyl.

3. The fused heterocycle compound or the pharmaceutically acceptable salt thereof according to claim 1, wherein $R^1$ is optionally substituted lower alkyl.

4. The fused heterocycle compound or the pharmaceutically acceptable salt thereof according to claim 1, wherein $R^1$ is tert-butyl.

5. The fused heterocycle compound or the pharmaceutically acceptable salt thereof according to claim 1, wherein $R^3$ is —C(=Z) $R^{4a}$ (wherein $R^{4a}$ represents optionally substituted lower alkyl, optionally substituted aryl, or an optionally substituted aliphatic heterocyclic group, and Z has the same definitions as described in claim 1), or is —C(=Z)NR$^5$R$^6$ (wherein $R^5$, $R^6$ and Z have the same definitions as described in claim 1, respectively).

6. The fused heterocycle compound or the pharmaceutically acceptable salt thereof according to claim 1, wherein $R^3$ is —C(=Z)NR$^5$R$^6$ (wherein $R^5$, $R^6$ and Z have the same definitions as described in claim 1, respectively).

7. The fused heterocycle compound or the pharmaceutically acceptable salt thereof according to claim 1, wherein $R^3$ is —C(=Z)NR$^{5a}$R$^{6a}$ (wherein $R^{5a}$ and $R^{6a}$ may be the same or different and each represents a hydrogen atom or optionally substituted lower alkyl or $R^{5a}$ and $R^{6a}$ together with the adjacent nitrogen atom thereto form an optionally substituted nitrogen-containing heterocyclic group).

8. The fused heterocycle compound or the pharmaceutically acceptable salt thereof according to claim 1, wherein Z is an oxygen atom.

9. The fused heterocycle compound or the pharmaceutically acceptable salt thereof according to claim 1, wherein n is 1.

10. The fused heterocycle compound or the pharmaceutically acceptable salt thereof according to claim 1, wherein $R^2$ is an optionally substituted aliphatic heterocyclic group.

11. The fused heterocycle compound or the pharmaceutically acceptable salt thereof according to claim 1, wherein W is a nitrogen atom.

12. The fused heterocycle compound or the pharmaceutically acceptable salt thereof according to claim 1, wherein W is CH.

13. A method for agonizing a CB2 receptor comprising administering an effective amount of the fused heterocycle compound or the pharmaceutically acceptable salt thereof according to claim 1 to a patient in need thereof.

14. A method for treating pain comprising administering an effective amount of the fused heterocycle compound or the pharmaceutically acceptable salt thereof according to claim 1 to a patient in need thereof.

* * * * *